US012667539B2

(12) United States Patent
Von Cosmos et al.

(10) Patent No.: US 12,667,539 B2
(45) Date of Patent: Jun. 30, 2026

(54) ORAL GUM COMPOSITION

(71) Applicant: NICOVENTURES TRADING LIMITED, London (GB)

(72) Inventors: Nicolas H. Von Cosmos, Moravian Falls, NC (US); Steven Lee Alderman, Lewisville, NC (US); Michael Zawadzki, Clemmons, NC (US)

(73) Assignee: Nicoventures Trading Limited, London (GB)

(*) Notice: Subject to any disclaimer, the term of this patent is extended or adjusted under 35 U.S.C. 154(b) by 274 days.

(21) Appl. No.: 17/955,891

(22) Filed: Sep. 29, 2022

(65) Prior Publication Data

US 2023/0098503 A1 Mar. 30, 2023

Related U.S. Application Data

(60) Provisional application No. 63/333,729, filed on Apr. 22, 2022, provisional application No. 63/250,619, filed on Sep. 30, 2021.

(51) Int. Cl.

| | |
|---|---|
| ***A61K 9/68*** | (2006.01) |
| ***A61K 31/465*** | (2006.01) |
| ***A61K 47/10*** | (2017.01) |
| ***A61K 47/12*** | (2006.01) |
| ***A61K 47/26*** | (2006.01) |
| ***A61K 47/36*** | (2006.01) |

(52) U.S. Cl.

CPC .......... *A61K 9/0058* (2013.01); *A61K 31/465* (2013.01); *A61K 47/10* (2013.01); *A61K 47/12* (2013.01); *A61K 47/26* (2013.01); *A61K 47/36* (2013.01)

(58) Field of Classification Search

CPC .... A61K 9/0058; A61K 31/465; A61K 47/10; A61K 47/12; A61K 47/26; A61K 47/36; A61K 9/0056; A23G 4/06; A23G 4/08; A23G 4/00; A24B 13/00; A24B 15/283

See application file for complete search history.

(56) References Cited

U.S. PATENT DOCUMENTS

| | | | |
|---|---|---|---|
| 5,417,229 | A | 5/1995 | Summers et al. |
| 6,138,683 | A | 10/2000 | Hersh et al. |
| 6,845,777 | B2 | 1/2005 | Pera |
| 6,958,143 | B2 | 10/2005 | Choi et al. |
| 7,032,601 | B2 | 4/2006 | Atchley et al. |
| 7,056,541 | B1 | 6/2006 | Stahl et al. |
| 7,507,427 | B2 | 3/2009 | Andersen et al. |
| 7,810,507 | B2 | 10/2010 | Dube et al. |
| 7,833,555 | B2 | 11/2010 | Andersen et al. |
| 7,861,728 | B2 | 1/2011 | Holton, Jr. et al. |
| 7,900,637 | B2 | 3/2011 | Fagerstrom et al. |
| 7,950,399 | B2 | 5/2011 | Winterson et al. |
| 8,069,861 | B2 | 12/2011 | Sinclair |
| 8,124,147 | B2 | 2/2012 | Cheng et al. |
| 8,293,295 | B2 | 10/2012 | Andersen et al. |
| 8,336,557 | B2 | 12/2012 | Kumar et al. |
| 8,343,532 | B2 | 1/2013 | Dam et al. |
| 8,424,541 | B2 | 4/2013 | Crawford et al. |
| 8,469,036 | B2 | 6/2013 | Williams et al. |
| 8,469,037 | B2 | 6/2013 | Liu et al. |
| 8,529,875 | B2 | 9/2013 | Andersen |
| 8,529,914 | B2 | 9/2013 | Fuisz et al. |
| 8,545,870 | B2 | 10/2013 | Dupinay et al. |
| 8,591,967 | B2 | 11/2013 | Andersen et al. |
| 8,613,285 | B2 | 12/2013 | Fuisz |
| 8,627,828 | B2 | 1/2014 | Strickland et al. |
| 8,642,016 | B2 | 2/2014 | Chau et al. |
| 8,714,163 | B2 | 5/2014 | Kumar et al. |
| 8,741,348 | B2 | 6/2014 | Hansson et al. |
| 8,747,562 | B2 | 6/2014 | Mishra et al. |
| 8,828,361 | B2 | 9/2014 | Anderson |
| 8,833,378 | B2 | 9/2014 | Axelsson et al. |
| 8,846,075 | B2 | 9/2014 | Johnson et al. |
| 8,858,984 | B2 | 10/2014 | Dam et al. |
| 8,863,755 | B2 | 10/2014 | Zhuang et al. |

(Continued)

FOREIGN PATENT DOCUMENTS

| | | |
|---|---|---|
| CN | 103005680 | 4/2013 |
| CN | 103263507 | 8/2013 |

(Continued)

OTHER PUBLICATIONS

Li, Qiaoyun, et al. "Investigating the role of ion-pair strategy in regulating nicotine release from patch: Mechanistic insights based on intermolecular interaction and mobility of pressure sensitive adhesive." European Journal of Pharmaceutical Sciences 119 (2018):102-111.) (Year: 2018).*

(Continued)

*Primary Examiner* — Robert A Wax

(74) *Attorney, Agent, or Firm* — Womble Bond Dickinson (US) LLP; Scott R. Breining

(57) ABSTRACT

The disclosure provides a composition configured for oral use. The composition includes a gum base, one or more bulking agents; an active ingredient having a basic amine functionality; and an organic acid, an alkali metal salt of an organic acid, or a combination thereof, wherein at least a portion the active ingredient having the basic amine functionality is associated with at least a portion of the organic acid or the alkali metal salt thereof, the association in the form of a basic amine-organic acid salt, an ion pair between the basic amine and a conjugate base of the organic acid, or both.

39 Claims, No Drawings

(56) References Cited

U.S. PATENT DOCUMENTS

| | | | |
|---|---|---|---|
| 8,871,243 | B2 | 10/2014 | Fankhauser et al. |
| 8,931,493 | B2 | 1/2015 | Sebastian et al. |
| 8,945,593 | B2 | 2/2015 | LoCoco et al. |
| 8,978,661 | B2 | 3/2015 | Atchley et al. |
| 8,992,974 | B2 | 3/2015 | McCarty |
| 9,027,567 | B2 | 5/2015 | Gee et al. |
| 9,039,839 | B2 | 5/2015 | Beeson et al. |
| 9,044,035 | B2 | 6/2015 | Jackson et al. |
| 9,084,439 | B2 | 7/2015 | Holton, Jr. |
| 9,155,321 | B2 | 10/2015 | Cantrell et al. |
| 9,161,567 | B2 | 10/2015 | Shikata et al. |
| 9,161,908 | B2 | 10/2015 | Nilsson |
| 9,167,835 | B2 | 10/2015 | Sengupta et al. |
| 9,185,931 | B2 | 11/2015 | Gao et al. |
| 9,204,667 | B2 | 12/2015 | Cantrell et al. |
| 9,237,768 | B2 | 1/2016 | Carroll et al. |
| 9,358,296 | B2 | 6/2016 | McCarty |
| 9,372,033 | B2 | 6/2016 | Lampe et al. |
| 9,386,800 | B2 | 7/2016 | Sebastian et al. |
| 9,402,414 | B2 | 8/2016 | Griscik et al. |
| 9,402,809 | B2 | 8/2016 | Axelsson et al. |
| 9,414,624 | B2 | 8/2016 | Carroll et al. |
| 9,420,825 | B2 | 8/2016 | Beeson et al. |
| 9,468,233 | B2 | 10/2016 | Macko et al. |
| 9,474,303 | B2 | 10/2016 | Holton, Jr. |
| 9,521,864 | B2 | 12/2016 | Gao et al. |
| 9,565,867 | B2 | 2/2017 | Wittorff et al. |
| 9,629,392 | B2 | 4/2017 | Holton, Jr. |
| 9,635,881 | B2 | 5/2017 | Sjögren et al. |
| 9,675,102 | B2 | 6/2017 | Hunt et al. |
| 9,763,928 | B2 | 9/2017 | Duggins et al. |
| 9,775,376 | B2 | 10/2017 | Cantrell et al. |
| 9,801,409 | B1 | 10/2017 | Smith |
| 9,848,634 | B2 | 12/2017 | Fuisz |
| 9,854,830 | B2 | 1/2018 | Gao et al. |
| 9,884,015 | B2 | 2/2018 | Gao et al. |
| 9,907,748 | B2 | 3/2018 | Borschke et al. |
| 9,925,145 | B2 | 3/2018 | Hubinette et al. |
| 9,930,909 | B2 | 4/2018 | Gao et al. |
| 9,999,243 | B2 | 6/2018 | Gao et al. |
| 10,039,309 | B2 | 8/2018 | Carroll et al. |
| 10,045,976 | B2 | 8/2018 | Fusco et al. |
| 10,092,715 | B2 | 10/2018 | Axelsson et al. |
| 10,130,120 | B2 | 11/2018 | Mishra et al. |
| 10,143,230 | B2 | 12/2018 | Mishra et al. |
| 10,149,850 | B2 | 12/2018 | Mishra et al. |
| 10,172,810 | B2 | 1/2019 | McCarty |
| 10,244,786 | B2 | 4/2019 | Gao et al. |
| 10,334,873 | B2 | 7/2019 | Mishra et al. |
| 10,357,054 | B2 | 7/2019 | Marshall et al. |
| 10,375,984 | B2 | 8/2019 | Hernandez Garcia et al. |
| 10,390,557 | B2 | 8/2019 | Börjesson et al. |
| 10,426,726 | B2 | 10/2019 | Neergaard |
| 10,463,070 | B2 | 11/2019 | Carroll et al. |
| 10,532,046 | B2 | 1/2020 | Rogers et al. |
| 10,543,205 | B2 | 1/2020 | Wittorff et al. |
| 2004/0118422 | A1 | 6/2004 | Lundin et al. |
| 2007/0031539 | A1 | 2/2007 | Calton |
| 2008/0081071 | A1 | 4/2008 | Sanghvi et al. |
| 2008/0166395 | A1 | 7/2008 | Roush |
| 2008/0248089 | A1* | 10/2008 | Bugge ...................... A23G 4/06 424/440 |
| 2009/0023819 | A1 | 1/2009 | Axelsson |
| 2009/0065013 | A1 | 3/2009 | Essen et al. |
| 2009/0253754 | A1 | 10/2009 | Selmin et al. |
| 2009/0301504 | A1 | 12/2009 | Worthen et al. |
| 2010/0004294 | A1 | 1/2010 | Axelsson et al. |
| 2010/0061940 | A1 | 3/2010 | Axelsson et al. |
| 2010/0187143 | A1 | 7/2010 | Essen et al. |
| 2010/0260690 | A1 | 10/2010 | Kristensen et al. |
| 2010/0294292 | A1 | 11/2010 | Hodin et al. |
| 2011/0139164 | A1 | 6/2011 | Mua et al. |
| 2011/0220130 | A1 | 9/2011 | Mua et al. |
| 2011/0268809 | A1 | 11/2011 | Brinkley et al. |
| 2012/0031415 | A1 | 2/2012 | Essen et al. |
| 2012/0037175 | A1 | 2/2012 | Cantrell et al. |
| 2013/0078307 | A1 | 3/2013 | Holton, Jr. et al. |
| 2013/0118512 | A1 | 5/2013 | Jackson et al. |
| 2013/0152953 | A1* | 6/2013 | Mua ....................... A24B 13/00 131/111 |
| 2013/0177646 | A1 | 7/2013 | Hugerth et al. |
| 2013/0206150 | A1 | 8/2013 | Duggins et al. |
| 2013/0251779 | A1 | 9/2013 | Svandal et al. |
| 2013/0289079 | A1* | 10/2013 | Chen .................... A61K 31/465 514/343 |
| 2013/0340773 | A1 | 12/2013 | Sebastian et al. |
| 2014/0130813 | A1 | 5/2014 | Strehle |
| 2014/0154301 | A1 | 6/2014 | Chau et al. |
| 2014/0255452 | A1 | 9/2014 | Reddick et al. |
| 2014/0264992 | A1 | 9/2014 | Miller et al. |
| 2015/0068544 | A1 | 3/2015 | Moldoveanu et al. |
| 2015/0068545 | A1 | 3/2015 | Moldoveanu et al. |
| 2015/0071972 | A1 | 3/2015 | Holton, Jr. et al. |
| 2015/0096573 | A1 | 4/2015 | Gao et al. |
| 2015/0096574 | A1 | 4/2015 | Gao et al. |
| 2015/0096576 | A1 | 4/2015 | Gao et al. |
| 2015/0296868 | A1 | 10/2015 | Sutton |
| 2016/0000140 | A1 | 1/2016 | Sebastian et al. |
| 2016/0073676 | A1 | 3/2016 | Cantrell et al. |
| 2016/0073689 | A1 | 3/2016 | Sebastian et al. |
| 2016/0157515 | A1 | 6/2016 | Chapman et al. |
| 2016/0192703 | A1 | 7/2016 | Sebastian et al. |
| 2017/0007594 | A1 | 1/2017 | Borschke |
| 2017/0164651 | A1 | 6/2017 | Mua et al. |
| 2017/0165252 | A1 | 6/2017 | Mua et al. |
| 2017/0172995 | A1 | 6/2017 | Repaka et al. |
| 2017/0280764 | A1 | 10/2017 | Sahlen et al. |
| 2017/0312261 | A1 | 11/2017 | Changoer et al. |
| 2017/0318858 | A1 | 11/2017 | Hodin et al. |
| 2018/0140007 | A1 | 5/2018 | Aspgren et al. |
| 2018/0140521 | A1 | 5/2018 | Geonnotti et al. |
| 2018/0140554 | A1 | 5/2018 | Wittorff |
| 2018/0153211 | A1 | 6/2018 | Persson |
| 2018/0235273 | A1 | 8/2018 | Carroll et al. |
| 2018/0255826 | A1 | 9/2018 | Persson et al. |
| 2018/0257801 | A1 | 9/2018 | Persson |
| 2019/0037909 | A1 | 2/2019 | Greenbaum et al. |
| 2019/0134207 | A1* | 5/2019 | Thorsen ............... A61K 9/0056 |
| 2019/0174812 | A1* | 6/2019 | Nielsen ................ A61K 9/0056 |
| 2019/0175581 | A1 | 6/2019 | Nielsen et al. |
| 2019/0255035 | A1 | 8/2019 | Bruun |
| 2020/0037638 | A1 | 2/2020 | Faraci et al. |
| 2020/0128870 | A1 | 4/2020 | Hassler et al. |
| 2020/0138706 | A1 | 5/2020 | Rudraraju et al. |
| 2020/0275689 | A1 | 9/2020 | Lewerenz |
| 2020/0297026 | A1 | 9/2020 | Kannisto et al. |
| 2020/0305496 | A1 | 10/2020 | Gessesse |
| 2020/0383372 | A1 | 12/2020 | Stahl et al. |
| 2020/0383373 | A1 | 12/2020 | Stahl et al. |
| 2021/0068447 | A1* | 3/2021 | Keller .................... A24B 15/10 |
| 2021/0386104 | A1* | 12/2021 | Shi ........................... A23G 3/48 |

FOREIGN PATENT DOCUMENTS

| | | | | | |
|---|---|---|---|---|---|
| CN | 103494324 | | | 1/2014 | |
| CN | 105192876 | | | 12/2015 | |
| CN | 105595404 | | | 5/2016 | |
| EP | 1474993 | A1 | * | 11/2004 | ........... A23G 3/0002 |
| WO | WO-2008090552 | A2 | * | 7/2008 | ............. A24B 13/00 |
| WO | WO2019/036243 | | | 2/2019 | |
| WO | WO-2021050741 | A1 | * | 3/2021 | ............. A24B 13/00 |

OTHER PUBLICATIONS

Robichaud Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.

* cited by examiner

ORAL GUM COMPOSITION

CROSS-REFERENCE TO RELATED APPLICATIONS

This application claims priority to U.S. Provisional Application No. 63/333,729, filed on Apr. 22, 2022, and to U.S. Provisional Application No. 63/250,619, filed on Sep. 30, 2021, each of which are incorporated herein by reference in their entirety and for all purposes.

FIELD OF THE DISCLOSURE

The present disclosure relates to an oral product. In particular, the present disclosure relates to compositions intended for human use. The compositions are configured for oral use and deliver substances such as flavors, active ingredients, or both during use.

BACKGROUND

Smokeless tobacco product configurations that combine tobacco material, nicotine components, and/or other active ingredients, with various binders and fillers have been proposed recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference. Oral products in similar formats and which are free of tobacco have also been proposed.

It would be desirable to provide products configured for oral use which are free of tobacco, and which may deliver active ingredients, flavorants, or both to the consumer in an enjoyable form.

BRIEF SUMMARY

The present disclosure generally provides a composition configured for oral use. The composition is in the form of a gum, for example, a chewing gum. The composition comprises a gum base including an elastomer, which is generally insoluble in an aqueous environment (e.g., in saliva). The composition further comprises a bulking agent and an active ingredient, and may further include flavoring agents and additional components as disclosed herein.

Accordingly, in one aspect is provided an oral composition comprising: a gum base; one or more bulking agents; an active ingredient having a basic amine functionality; and an organic acid, an alkali metal salt of an organic acid, or a combination thereof, wherein at least a portion the active ingredient having the basic amine functionality is associated with at least a portion of the organic acid or the alkali metal salt thereof, the association in the form of a basic amine-organic acid salt, an ion pair between the basic amine and a conjugate base of the organic acid, or both.

In some embodiments, the oral composition is in the form of a chewing gum.

In some embodiments, at least a portion the active ingredient having the basic amine functionality is in the form of an ion pair between the basic amine and a conjugate base of the organic acid.

In some embodiments, the organic acid has a log P value of from about 1 to about 12. In some embodiments, wherein the organic acid has a log P value of from about 1.4 to about 4.5. In some embodiments, the organic acid has a log P value of from about 2.5 to about 3.5. In some embodiments, the organic acid has a log P value of from about 4.5 to about 12, and the composition further comprises a solubility enhancer. In some embodiments, the solubility enhancer is glycerol or propylene glycol.

In some embodiments, the oral composition comprises from about 0.05, about 0.1, about 1, about 1.5, about 2, or about 5, to about 10, about 15, or about 20 molar equivalents of the organic acid, the alkali metal salt thereof, or the combination thereof, relative to the active ingredient having a basic amine functionality, calculated as the amine free base. In some embodiments, the oral composition comprises from about 2 to about 10 molar equivalents of the organic acid, the alkali metal salt thereof, or the combination thereof, relative to the active ingredient having a basic amine functionality, calculated as the amine free base.

In some embodiments, the organic acid comprises benzoic acid, a menthyl or tocopherol monoester of a dicarboxylic acid, or a combination thereof. In some embodiments, the dicarboxylic acid is malonic acid, succinic acid, glutaric acid, adipic acid, fumaric acid, maleic acid, or a combination thereof.

In some embodiments, the organic acid comprises tocopherol succinate, monomenthyl succinate, monomenthyl fumarate, monomenthyl glutarate, or a combination thereof. In some embodiments, the oral composition further comprises benzoic acid and sodium benzoate.

In some embodiments, the oral composition comprises the organic acid and an alkali metal salt of the organic acid. In some embodiments, a ratio of the organic acid to the alkali metal salt of the organic acid is from about 0.1 to about 10.

In some embodiments, the alkali metal is sodium or potassium.

In some embodiments, the oral composition comprises benzoic acid and sodium benzoate.

In some embodiments, the pH of the composition is from about 4.0 to about 9.0. In some embodiments, the pH of the composition is from about 4.5 to about 7. In some embodiments, the pH of the composition is from about 5.5 to about 7. In some embodiments, the pH of the composition is from about 4.0 to about 5.5. In some embodiments, the pH of the composition is from about 7.0 to about 9.0.

In some embodiments, the active ingredient having a basic amine functionality is nicotine. In some embodiments, the nicotine is present in an amount of from about 0.001 to about 10% by weight of the composition, calculated as the free base and based on the total weight of the composition. In some embodiments, the oral composition the oral composition comprises nicotine benzoate, nicotine polacrilex, or a combination thereof.

In some embodiments, the gum base comprises a synthetic elastomer. In some embodiments, the gum base further comprises a plasticizer, a filler, a softener, an emulsifier, a wax, an anti-tacking agent, an antioxidant, or a combination thereof.

In some embodiments, the bulking agent comprises one or more sugar alcohols. In some embodiments, the oral composition comprises, as the bulking agent, a combination of: sorbitol in an amount from about 25 to about 50% by weight;

maltitol in an amount from about 10 to about 20% by weight; and isomalt in an amount from about 10 to about 20% by weight, each based on the total weight of the oral composition.

In some embodiments, the oral composition further comprises one or more additional active ingredients, one or more flavoring agents, one or more salts, one or more sweeteners, one or more humectants, a tobacco material, or combinations thereof.

In some embodiments, the oral composition further comprises one or more additional active ingredients selected from the group consisting of nutraceuticals, botanicals, stimulants, amino acids, vitamins, cannabinoids, cannabimimetics, and terpenes.

In some embodiments, the oral composition comprises: the gum base in an amount from about 20 to about 30% by weight, based on the total weight of the oral composition; the bulking agent in an amount from about 50 to about 80% by weight, based on the total weight of the oral composition, wherein the bulking agent comprises one or more sugar alcohols; a humectant in an amount from about 1 to about 2% by weight, based on the total weight of the oral composition; nicotine benzoate; and sodium benzoate.

In some embodiments, the oral composition comprises: the gum base in an amount from about 20 to about 30% by weight, based on the total weight of the oral composition; the bulking agent in an amount from about 50 to about 80% by weight, based on the total weight of the oral composition, wherein the bulking agent comprises one or more sugar alcohols; a humectant in an amount from about 1 to about 2% by weight, based on the total weight of the oral composition; nicotine benzoate; nicotine polacrilex; and sodium benzoate.

In some embodiments, the oral composition comprises: the gum base in an amount from about 20 to about 30% by weight, based on the total weight of the oral composition; the bulking agent in an amount from about 50 to about 80% by weight, based on the total weight of the oral composition, wherein the bulking agent comprises one or more sugar alcohols; a humectant in an amount from about 1 to about 2% by weight, based on the total weight of the oral composition; nicotine polacrilex; and sodium benzoate.

In some embodiments, the oral composition further comprises flavor granules. In some embodiments, the flavor granules comprise: a sugar alcohol in an amount by weight from about 60 to about 90%; a humectant in an amount by weight from about 16 to about 22%; a sweetener in an amount by weight from about 0.1 to about 0.5%; a filler in an amount by weight from about 1 to about 3%; a colorant; and a flavorant, wherein each amount by weight is based on the total weight of the flavor granules. In some embodiments, the sugar alcohol is isomalt, the humectant is glycerin, the sweetener is sucralose, and the filler is microcrystalline cellulose.

In some embodiments, the flavor granules comprise a sugar alcohol in an amount by weight from about 15 to about 35%; a humectant in an amount by weight from about 15 to about 30%; a sweetener in an amount by weight from about 0.1 to about 0.5%; a filler in an amount by weight from about 20 to about 50%; a flavorant in an amount by weight from about 20 to about 30%; and a colorant; wherein each amount by weight is based on the total weight of the flavor granules. In some embodiments, the sugar alcohol is isomalt, the humectant is glycerin, the sweetener is sucralose, and the filler is microcrystalline cellulose.

In some embodiments, the flavor granules comprise a combination of two sugar alcohols in a total amount by weight from about 96 to about 99%; a sweetener in an amount by weight from about 0.1 to about 0.5%; a flavorant in an amount by weight from about 0.1 to about 1%; and a colorant in an amount by weight from about 0.1 to about 1.5%, wherein each amount by weight is based on the total weight of the flavor granules. In some embodiments, the flavor granules consist of isomalt in an amount by weight from about 92 to about 96%; maltitol syrup in an amount by weight from about 4 to about 6%; sucralose in an amount by weight from about 0.1 to about 0.5%; and with the balance consisting of colorant and flavorant.

The disclosure includes, without limitations, the following embodiments.

Embodiment 1: An oral composition comprising: a gum base; one or more bulking agents; an active ingredient having a basic amine functionality; and an organic acid, an alkali metal salt of an organic acid, or a combination thereof, wherein at least a portion the active ingredient having the basic amine functionality is associated with at least a portion of the organic acid or the alkali metal salt thereof, the association in the form of a basic amine-organic acid salt, an ion pair between the basic amine and a conjugate base of the organic acid, or both.

Embodiment 2: The oral composition of embodiment 1, in the form of a chewing gum.

Embodiment 3: The oral composition of embodiment 1 or 2, wherein at least a portion the active ingredient having the basic amine functionality is in the form of an ion pair between the basic amine and a conjugate base of the organic acid.

Embodiment 4: The oral composition of any one of embodiments 1-3, wherein the organic acid has a log P value of from about 1 to about 12.

Embodiment 5: The oral composition of any one of embodiments 1-4, wherein the organic acid has a log P value of from about 1.4 to about 4.5.

Embodiment 6: The oral composition of any one of embodiments 1-5, wherein the organic acid has a log P value of from about 2.5 to about 3.5.

Embodiment 7: The oral composition of any one of embodiments 1-6, wherein the organic acid has a log P value of from about 4.5 to about 12, and wherein the composition further comprises a solubility enhancer.

Embodiment 8: The oral composition of embodiment 7, wherein the solubility enhancer is glycerol or propylene glycol.

Embodiment 9: The oral composition of any one of embodiments 1-8, comprising from about 0.05, about 0.1, about 1, about 1.5, about 2, or about 5, to about 10, about 15, or about 20 molar equivalents of the organic acid, the alkali metal salt thereof, or the combination thereof, relative to the active ingredient having a basic amine functionality, calculated as the amine free base.

Embodiment 10: The oral composition of any one of embodiments 1-9, comprising from about 2 to about 10 molar equivalents of the organic acid, the alkali metal salt thereof, or the combination thereof, relative to the active ingredient having a basic amine functionality, calculated as the amine free base.

Embodiment 11: The oral composition of any one of embodiments 1-10, wherein the organic acid comprises benzoic acid, a menthyl or tocopherol monoester of a dicarboxylic acid, or a combination thereof.

Embodiment 12: The oral composition of any one of embodiments 1-11, wherein the dicarboxylic acid is malonic acid, succinic acid, glutaric acid, adipic acid, fumaric acid, maleic acid, or a combination thereof.

Embodiment 13: The oral composition of any one of embodiments 1-12, wherein the organic acid comprises tocopherol succinate, monomenthyl succinate, monomenthyl fumarate, monomenthyl glutarate, or a combination thereof.

Embodiment 14: The oral composition of any one of embodiments 1-13, further comprising benzoic acid and sodium benzoate.

Embodiment 15: The oral composition of any one of embodiments 1-14, comprising benzoic acid and sodium benzoate.

Embodiment 16: The oral composition of any one of embodiments 1-15, comprising the organic acid and an alkali metal salt of the organic acid.

Embodiment 17: The oral composition of any one of embodiments 1-16, wherein the alkali metal is sodium or potassium.

Embodiment 18: The oral composition of any one of embodiments 1-17, wherein a ratio of the organic acid to the alkali metal salt of the organic acid is from about 0.1 to about 10.

Embodiment 19: The oral composition of any one of embodiments 1-18, wherein the pH of the composition is from about 4.0 to about 9.0.

Embodiment 20: The oral composition of any one of embodiments 1-19, wherein the pH of the composition is from about 4.5 to about 7.

Embodiment 21: The oral composition of any one of embodiments 1-20, wherein the pH of the composition is from about 5.5 to about 7.

Embodiment 22: The oral composition of any one of embodiments 1-21, wherein the pH of the composition is from about 4.0 to about 5.5.

Embodiment 23: The oral composition of any one of embodiments 1-22, wherein the pH of the composition is from about 7.0 to about 9.0.

Embodiment 24: The oral composition of any one of embodiments 1-23, wherein the active ingredient having a basic amine functionality is nicotine.

Embodiment 25: The oral composition of any one of embodiments 1-24, wherein the nicotine is present in an amount of from about 0.001 to about 10% by weight of the composition, calculated as the free base and based on the total weight of the composition.

Embodiment 26: The oral composition of any one of embodiments 1-25, wherein the oral composition comprises a nicotine salt (e.g., nicotine benzoate), nicotine polacrilex, or a combination thereof.

Embodiment 27: The oral composition of any one of embodiments 1-26, wherein the gum base comprises a synthetic elastomer.

Embodiment 28: The oral composition of any one of embodiments 1-27, wherein the gum base further comprises a plasticizer, a filler, a softener, an emulsifier, a wax, an anti-tacking agent, an antioxidant, or a combination thereof.

Embodiment 29: The oral composition of any one of embodiments 1-28, wherein the bulking agent comprises one or more sugar alcohols.

Embodiment 30: The oral composition of any one of embodiments 1-29, wherein the oral composition comprises, as the bulking agent, a combination of: sorbitol in an amount from about 25 to about 50% by weight; maltitol in an amount from about 10 to about 20% by weight; and isomalt in an amount from about 10 to about 20% by weight, each based on the total weight of the oral composition.

Embodiment 31: The oral composition of any one of embodiments 1-30, further comprising one or more additional active ingredients, one or more flavoring agents, one or more salts, one or more sweeteners, one or more humectants, a tobacco material, or combinations thereof.

Embodiment 32: The oral composition of any one of embodiments 1-31, further comprising one or more additional active ingredients selected from the group consisting of nutraceuticals, botanicals, stimulants, amino acids, vitamins, cannabinoids, cannabimimetics, and terpenes.

Embodiment 33: The oral composition of any one of embodiments 1-32, comprising: the gum base in an amount from about 20 to about 30% by weight, based on the total weight of the oral composition; the bulking agent in an amount from about 50 to about 80% by weight, based on the total weight of the oral composition, wherein the bulking agent comprises one or more sugar alcohols; a humectant in an amount from about 1 to about 2% by weight, based on the total weight of the oral composition; nicotine benzoate; and sodium benzoate (or other alkali metal benzoate).

Embodiment 34: An oral composition comprising: a gum base; one or more bulking agents; an active ingredient having a basic amine functionality; and an organic acid, wherein the organic acid comprises benzoic acid, a menthyl or tocopherol monoester of a dicarboxylic acid, or a combination thereof, such as a dicarboxylic acid selected from malonic acid, succinic acid, glutaric acid, adipic acid, fumaric acid, maleic acid, or a combination thereof, and in particular, wherein the organic acid comprises tocopherol succinate, monomenthyl succinate, monomenthyl fumarate, monomenthyl glutarate, or a combination thereof.

Embodiment 35: The oral composition of embodiment 34, wherein the active ingredient having the basic amine functionality is nicotine.

Embodiment 36: The oral composition of embodiment 35, wherein the nicotine comprises a nicotine salt, nicotine polacrilex, or a combination thereof.

Embodiment 37: The oral composition of any one of embodiments 34-36, comprising nicotine benzoate.

Embodiment 38: The oral composition of any one of embodiments 34-37, comprising nicotine polacrilex.

Embodiment 39: The oral composition of any one of embodiments 34-38, comprising a combination of nicotine benzoate and nicotine polacrilex.

Embodiment 40: The oral composition of claim 1, comprising: the gum base in an amount from about 20 to about 30% by weight, based on the total weight of the oral composition; the bulking agent in an amount from about 50 to about 80% by weight, based on the total weight of the oral composition, wherein the bulking agent comprises one or more sugar alcohols; a humectant in an amount from about 1 to about 2% by weight, based on the total weight of the oral composition; nicotine polacrilex; and sodium benzoate.

Embodiment 41: The oral composition of any one of embodiments 1-40, further comprising flavor granules.

Embodiment 42: The oral composition of embodiment 41, wherein the flavor granules comprise: a sugar alcohol in an amount by weight from about 60 to about 90%; a humectant in an amount by weight from about 16 to about 22%; a sweetener in an amount by weight from about 0.1 to about 0.5%; a filler in an amount by weight from about 1 to about 3%; a colorant; and a flavorant, wherein each amount by weight is based on the total weight of the flavor granules.

Embodiment 43: The oral composition of embodiment 42, wherein the sugar alcohol is isomalt, the humectant is glycerin, the sweetener is sucralose, and the filler is microcrystalline cellulose.

Embodiment 44: The oral composition of embodiment 41, wherein the flavor granules comprise: a sugar alcohol in an amount by weight from about 15 to about 35%; a humectant in an amount by weight from about 15 to about 30%; a sweetener in an amount by weight from about 0.1 to about 0.5%; a filler in an amount by weight from about 20 to about 50%; a flavorant in an amount by weight from about 20 to about 30%; and a colorant; wherein each amount by weight is based on the total weight of the flavor granules.

Embodiment 45: The oral composition of embodiment 44, wherein the sugar alcohol is isomalt, the humectant is glycerin, the sweetener is sucralose, and the filler is microcrystalline cellulose.

Embodiment 46: The oral composition of embodiment 41, wherein the flavor granules comprise: a combination of two sugar alcohols in a total amount by weight from about 96 to about 99%; a sweetener in an amount by weight from about 0.1 to about 0.5%; a flavorant in an amount by weight from about 0.1 to about 1%; and a colorant in an amount by weight from about 0.1 to about 1.5%, wherein each amount by weight is based on the total weight of the flavor granules.

Embodiment 47: The oral composition of embodiment 46, wherein the granules consist of isomalt in an amount by weight from about 92 to about 96%; maltitol syrup in an amount by weight from about 4 to about 6%; sucralose in an amount by weight from about 0.1 to about 0.5%; and with the balance consisting of colorant and flavorant.

These and other features, aspects, and advantages of the disclosure will be apparent from a reading of the following detailed description. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements.

As used in this specification and the claims, the singular forms "a," "an," and "the" include plural referents unless the context clearly dictates otherwise.

The term "about" used throughout this specification is used to describe and account for small fluctuations. For example, the term "about" can refer to less than or equal to +10%, such as less than or equal to +5%, less than or equal to +2%, less than or equal to +1%, less than or equal to +0.5%, less than or equal to ±0.2%, less than or equal to +0.1% or less than or equal to +0.05%. All numeric values herein are modified by the term "about," whether or not explicitly indicated. A value modified by the term "about" of course includes the specific value. For instance, "about 5.0" must include 5.0.

Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

Oral Composition

As described herein, there is provided an oral composition comprising a gum base; one or more bulking agents; an active ingredient having a basic amine functionality; and an organic acid, an alkali metal salt of an organic acid, or a combination thereof. The oral composition may further comprise additional active ingredients, flavoring agents, salts, sweeteners, humectants, a tobacco material, or combinations thereof. The relative amounts of the various components within the composition may vary, and typically are selected so as to provide the desired sensory and performance characteristics to the oral composition. The example individual components of the oral composition and characteristics of the oral composition are each described herein below.

Gum Base

The oral composition as disclosed herein comprises a gum base. By the term "gum base" is meant the generally water-insoluble and hydrophobic ingredients that provide the desired texture to the oral composition. The oral composition may comprise the gum base in an amount from about 5 to about 95 percent by weight, based on the total weight of the oral composition, such as in an amount from about 5, about 10, about 15, about 20, about 25, about 30, about 35, about 40, about 45, or about 50, to about 55, about 60, about 65, about 70, about 75, about 80, about 85, about 90, or about 95% by weight, based on the total weight of the oral composition. In some embodiments, the oral composition comprises the gum base in an amount from about 10 to about 60 percent by weight, such as about 10, about 15, about 20, about 25, about 30, about 35, about 40, about 45, about 50, about 55, or about 60 percent by weight, based on the total weight of the oral composition. In some embodiments, the oral composition comprises the gum base in an amount from about 15 to about 40, or from about 20 to about 30 percent by weight, based on the total weight of the oral composition.

The formulation of the gum base can vary substantially depending on the particular oral composition to be prepared and on the desired masticatory and other sensory characteristics of the final oral composition (e.g., hardness and elasticity, as well as more subjective parameters related to the chew-feel experienced by a user). Generally, the gum base comprises an elastomer. Elastomers provide the rubbery, cohesive nature to the gum base and the overall oral composition. This rubbery, cohesive nature may vary depending on the elastomer's chemical structure and how it is compounded with other ingredients in the gum base and the overall oral composition. Accordingly, the elastomer employed in the gum base may vary depending upon various factors such as the type of gum base desired, the desired texture of the gum, and the other components used to make the final oral composition. Generally, the elastomer may be any water-insoluble polymer known in the art. Elastomers suitable for use in the gum base of the present invention may include natural, synthetic, or a combination thereof.

In some embodiments, the elastomer is a natural elastomer. Non-limiting examples of suitable natural elastomers include latex, chicle, crown gum, nispero, rosidinha, jelutong, perillo, niger gutta, tunu, balata, guttapercha, lechi caspi, sorva, gutta kay, massaranduba balata, massaranduba chocolate, nispero, rosindinha, gutta hang kang, chiquibul, pendare, leche de vaca, tunu, chilte, and mixtures thereof.

In some embodiments, the elastomer is a synthetic elastomer. Non-limiting examples of suitable synthetic elastomers include styrene-butadiene copolymers (SBR), polyisobutylene, isobutylene-isoprene copolymers, polyethylene, polyvinyl acetate, biodegradable polymers, and mixtures thereof. Further examples of synthetic elastomers include, but are not limited to, synthetic elastomers listed in Food and Drug Administration, CFR, Title 21, Section 172,615, the Masticatory Substances, Synthetic. In some embodiments, the synthetic elastomer is biodegradable, for example, a lactic acid polymer. In some embodiments, the synthetic elastomer is a polyisobutylene having a gel permeation chromatography (GPC) average molecular weight in the range of about 10,000 to 1,000,000, such as about 50,000 to 80,000. In some embodiments, the synthetic elastomer is an isobutylene-isoprene copolymer, a styrene-butadiene copolymer (e.g., having a styrene-butadiene ratio of about 1:3 to 3:1), or a polyvinyl acetate (PVA) polymer. Suitable isobutylene-isoprene copolymers, styrene-butadiene copolymers, and polyvinyl acetate polymers may have a GPC average molecular weight in a range from about 2,000 to 90,000, such as from about 3,000 to about 80,000, or from about 30,000 to about 50,000.

In some embodiments, a synthetic elastomer having a high molecular weight and a synthetic elastomer having a low molecular weight are combined. Examples of such combinations are polyisobutylene and styrene-butadiene copolymer, polyisobutylene and polyisoprene copolymer, polyisobutylene and isobutylene-isoprene copolymer, and combinations thereof. Any of the foregoing individual synthetic polymers may further comprise polyvinyl acetate, vinyl acetate-vinyl laurate copolymers, biodegradable polymers, and mixtures thereof.

Gum bases, and particularly synthetic elastomer-based gum bases, may further comprise one or more of plasticizers, fillers, softeners, emulsifiers, waxes, anti-tacking agents, and further miscellaneous components such as antioxidants, colorants, flavoring agents, buffers, and the like.

In some embodiments, the gum base comprises a plasticizer. Plasticizers vary the firmness and flexibility of the gum base by virtue of interrupting intermolecular polymer chains to varying degrees. Suitable plasticizers include natural resins, synthetic resins, waxes, and combinations thereof. Natural resins include, but are not limited to, natural terpene resins and natural rosin esters, often referred to as ester gums. Non-limiting examples of natural rosin esters include glycerol esters of partially hydrogenated rosins, glycerol esters of polymerized rosins, glycerol esters of partially dimerized rosins, glycerol esters of tall oil rosins, pentaerythritol esters of partially hydrogenated rosins, methyl esters of rosins, partially hydrogenated methyl esters of rosins, and pentaerythritol esters of rosins. Synthetic resins include, but are not limited to, terpene resins derived from alpha-pinene, beta-pinene, and/or d-limonene.

In some embodiments, the gum base comprises a wax. Examples of suitable waxes include, but are not limited to, microcrystalline wax, rice wax, carnauba wax. bees wax, rice bran wax, and candellila wax.

In some embodiments, the gum base comprises a filler. Suitable fillers include, but are not limited to, magnesium carbonate, calcium carbonate, ground limestone, silicates, such as magnesium and aluminum silicate, clay, alumina, talc, titanium oxide, mono-, di- and tri-calcium phosphate, cellulose polymers, and combinations thereof. In particular embodiments, the filler is calcium carbonate, talc, or a combination thereof. In one particular embodiment, the filler is talc.

In some embodiments, the gum base comprises an emulsifier. Certain emulsifiers may further serve as softeners. Suitable emulsifiers and/or softeners include, but are not limited to, tallow, hydrogenated tallow, hydrogenated and partially hydrogenated vegetable oils, cocoa butter, glycerol monostearate, glycerol acetate, glycerol diacetate (diacetin) glycerol triacetate (triacetin), lecithin, mono-, di- and triglycerides, acetylated monoglycerides, fatty acids (e.g. stearic, palmitic, oleic and linoleic acids), sorbitan fatty acid esters, lanolin, and combinations thereof.

In some embodiments, the gum base comprises an antioxidant. Examples of suitable antioxidants include, but are not limited to, butylated hydroxyanisole (BHA), butylated hydroxy-toluene (BHT), tertiary butyl hydroquinone (TBHQ), tocopherols, mixed tocopherols, eugenol, gum guaiac, thymol, carvacrol, spice extracts of thyme, oregano, rosemary, nutmeg, ginger, and mixtures thereof.

The quantity of each individual component of the gum base may vary. Typical ranges of the aforementioned gum base components, expressed in % by weight and based on the total weight of the gum base, are: from about 5 to about 80% elastomer; from about 1 to about 80% of plasticizer; from about 0 to about 40% wax, from about 0 to about 35% emulsifier/softener; from about 0 to about 50% filler; and from about 0 to 5% of other miscellaneous ingredients (antioxidants, colorants, and the like).

In some embodiments, the gum base comprises a mixture of elastomeric polymers, resins, refined waxes, glycerol esters of edible fatty acids, talc, and an antioxidant, each as described herein above. One particularly suitable example of such a gum base is available as Artica T, available from CAFOSA Gum S/A, Barcelona, Spain.

Bulking Agent

The oral composition as disclosed herein comprises one or more bulking agents. Such bulking agents are generally at least partially water soluble, and may be entirely water soluble. Bulking agents may serve more than one purpose. For example, bulking agents may act as fillers (i.e., providing physical bulk to the composition), as sweeteners, and as texture modifiers (e.g., contributing to physical attributes such as chewiness, firmness, softness, and the like). Suitable bulking agents include sweeteners such as sugars, sugar alcohols, and combinations thereof. Sugars generally include saccharide-containing components (e.g., mono- and disaccharides or polysaccharides). Suitable sugars include, but are not limited to, gluctose, sucrose, dextrose, lactose, maltose, isomaltulose, dried invert sugar, fructose, levulose, galactose, corn syrup solids, high maltose syrup, invert/high fructose syrup, maltotriose, erythrose, xylose, leucrose, mannose, and L-sugars. Sugar alcohols are polyols derived from monosaccharides or disaccharides that have a partially or fully hydrogenated form (e.g., hydrogenated starch hydrolysates). Sugar alcohols have, for example, about 4 to about 20 carbon atoms and include erythritol, arabitol, ribitol, isomalt, maltitol, dulcitol, iditol, mannitol, xylitol, lactitol, and sorbitol.

In some embodiments, the bulking agent comprises one or more sugar alcohols. In some embodiments, the one or more sugar alcohols are selected from the group consisting of erythritol, arabitol, ribitol, isomalt, maltitol, dulcitol, iditol, mannitol, xylitol, lactitol, sorbitol, and combinations thereof. In some embodiments, the one or more sugar alcohols are selected from the group consisting of isomalt, maltitol, mannitol, sorbitol, and combinations thereof. In particular embodiments, the bulking agent is a combination of sorbitol, maltitol, and isomalt. Isomalt is an equimolar mixture of two disaccharides, each composed of two sugars as follows: glucose and mannitol (α-D-glucopyranosido-1,6-mannitol); and glucose and sorbitol (α-D-glucopyranosido-1,6-sorbitol). In some embodiments, the isomalt is in crystalline form. Crystalline isomalt is commercially available, or may be prepared from isomalt by heating (e.g., to a temperature greater than about 130° C., or greater than about 160° C.) prior to crystallization according to known methods.

The quantity of bulking agent may vary depending on the gum base used and the quantity thereof, as well as the desired chewiness, sweetness, and the like. Generally, the oral composition comprises the bulking agent in an amount from about 5 to about 95% by weight of the oral composition, such as from about 10 to about 90%, from about 30 to about 90%, or from about 40 to about 90% by weight, based on the total weight of the oral composition. In particular embodiments, the oral composition comprises sorbitol in an amount from about 25 to about 50% by weight, maltitol in an amount from about 10 to about 20% by weight, and isomalt in an amount from about 10 to about 20% by weight, based on the total weight of the oral composition.

Active Ingredient

The oral composition as disclosed herein comprises an active ingredient. As used herein, an "active ingredient" refers to one or more substances belonging to any of the following categories: API (active pharmaceutical substances), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods". These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular oral product.

The particular percentages of active ingredients present will vary depending upon the desired characteristics of the particular oral product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition. Further suitable ranges for specific active ingredients are provided herein below.

Nicotine Component

In certain embodiments, the active ingredient comprises a nicotine component. By "nicotine component" is meant any suitable form of nicotine (e.g., free base or salt) for providing oral absorption of at least a portion of the nicotine present. The source of the nicotine may vary, and may be natural or synthetic. Nicotine may be tobacco-derived (e.g., a tobacco extract) or non-tobacco derived (e.g., synthetic or otherwise obtained). Most preferably, the nicotine is naturally occurring and obtained as an extract from a *Nicotiana* species (e.g., tobacco). The nicotine can have the enantiomeric form S(−)-nicotine, R(+)-nicotine, or a mixture of S(−)-nicotine and R(+)-nicotine. Most preferably, the nicotine is in the form of S(−)-nicotine (e.g., in a form that is virtually all S(−)-nicotine) or a racemic mixture composed primarily or predominantly of S(−)-nicotine (e.g., a mixture composed of about 95 weight parts S(−)-nicotine and about 5 weight parts R(+)-nicotine). Most preferably, the nicotine is employed in virtually pure form or in an essentially pure form. Highly preferred nicotine that is employed has a purity of greater than about 95 percent, more preferably greater than about 98 percent, and most preferably greater than about 99 percent, on a weight basis.

Typically, the nicotine component is selected from the group consisting of nicotine free base and a nicotine salt. In some embodiments, the nicotine component is nicotine in its free base form, which easily can be adsorbed in for example, a microcrystalline cellulose material to form a microcrystalline cellulose-nicotine carrier complex. See, for example, the discussion of nicotine in free base form in US Pat. Pub. No. 2004/0191322 to Hansson, which is incorporated herein by reference.

In some embodiments, at least a portion of the nicotine component can be employed in the form of a salt. Salts of nicotine can be provided using the types of ingredients and techniques set forth in U.S. Pat. No. 2,033,909 to Cox et al. and Perfetti, *Beitrage Tabakforschung Int.,* 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride. In some embodiments, the nicotine component is nicotine bitartrate.

In some embodiments, at least a portion of the nicotine can be in the form of a resin complex of nicotine, where nicotine is bound in an ion-exchange resin, such as nicotine polacrilex, which is nicotine bound to, for example, a polymethacrylic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

In some embodiments, at least a portion of the nicotine component can be ion paired as described further herein below.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the composition. The total amount of nicotine present may be provided by more than one source of nicotine, such as various combinations of any of nicotine free base, nicotine salt, ion paired nicotine, and polymer-bound nicotine (e.g., nicotine polacrilex). In some embodiments, the nicotine component is nicotine benzoate, nicotine polacrilex, or a mixture thereof.

In some embodiments, the oral products or compositions of the disclosure can be characterized as completely free or substantially free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). The botanical materials used in the present invention may comprise, without limitation, any of the compounds and sources set forth herein, including mixtures thereof. Certain botanical materials of this type are sometimes referred to as dietary supplements, nutraceuticals, "phytochemicals" or "functional foods."

When present, a botanical is typically at a concentration of from about 0.01% w/w to about 10% by weight, such as, e.g., from about from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein.

Non-limiting examples of non-tobacco botanical materials include without limitation acai berry (*Euterpe oleracea martius*), acerola (*Malpighia glabra*), alfalfa, allspice, *Angelica* root, anise (e.g., star anise), annatto seed, apple (*Malus domestica*), apricot oil, ashwagandha, *Bacopa monniera*, baobab, basil (*Ocimum basilicum*), bay, bee balm, beet root, bergamot, blackberry (*Morus nigra*), black cohosh, black pepper, black tea, blueberries, boldo (*Peumus boldus*), borage, bugleweed, cacao, calamus root, camu (*Myrcaria dubia*), *Cannabis*/hemp, caraway seed, cardamom, cassis, catnip, catuaba, cayenne pepper, *Centella asiatica*, chaga mushroom, Chai-hu, chamomile, cherry, chervil, chive, chlorophyll, chocolate, cilantro, cinnamon (*Cinnamomum cassia*), citron grass (*Cymbopogon citratus*), citrus, clary sage, cloves, coconut (*Cocos nucifera*), coffee, comfrey leaf and root, *cordyceps*, coriander seed, cranberry, cumin, curcumin, damiana, dandelion, *Dorstenia arifolia, Dorstenia odorata, Echinacea*, elderberry, elderflower, endro (*Anethum graveolens*), evening primrose, eucalyptus, fennel, feverfew, flax, *Galphimia glauca*, garlic, ginger (*Zingiber officinale*), gingko biloba, ginseng, goji berries, goldenseal, grape seed, grapefruit, grapefruit rose (*Citrus paradisi*), graviola (*Annona muricata*), green tea, guarana, gutu kola, hawthorn, hazel, hemp, hibiscus flower (*Hibiscus sabdariffa*), honeybush, hops, jiaogulan, jambu (*Spilanthes oleraceae*), jasmine (*Jasminum officinale*), juniper berry (*Juniperus communis*), Kaempferia *parviflora* (Thai ginseng), kava, laurel, lavender, lemon (*Citrus limon*), lemon balm, lemongrass, licorice, lilac, Lion's mane, lutein, maca (*Lepidium meyenii*), mace, marjoram, matcha, milk thistle, mints (menthe), mulberry, *Nardostachys chinensis*, nutmeg, olive, oolong tea, orange (*Citrus sinensis*), oregano, papaya, paprika, pennyroyal, peppermint (*Mentha piperita*), pimento, potato peel, primrose, quercetin, quince, red clover, resveratrol, Rhizoma gastrodiae, *Rhodiola*, rooibos (red or green), rosehip (*Rosa canina*), rosemary, saffron, sage, Saint John's Wort, sandalwood, salvia (*Salvia officinalis*), savory, saw palmetto, *Sceletium tortuosum*, Schisandra, *Silybum marianum*, Skullcap, spearmint, Spikenard, spirulina, slippery elm bark, sorghum bran hi-tannin, sorghum grain hi-tannin, spearmint (*Mentha spicata*), spirulina, star anise, sumac bran, tarragon, thyme, tisanes, turmeric, *Turnera aphrodisiaca, Uva ursi*, valerian, vanilla, *Viola odorata*, wild yam root, wintergreen, *Withania somnifera*, yacon root, yellow dock, yerba mate, and yerba santa.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the active ingredient is caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Amino Acids

In some embodiments, the active ingredient comprises an amino acid. As used herein, the term "amino acid" refers to an organic compound that contains amine ($—NH_2$) and carboxyl (—COOH) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-translational modification). Non-limiting examples of non-proteinogenic amino acids include gamma-aminobutyric acid (GABA), taurine (2-aminoethanesulfonic acid), theanine (L-γ-glutamylethylamide), hydroxyproline, and beta-alanine.

When present, an amino acid or combination of amino acids (e.g., taurine, theanine, and combinations thereof) is typically at a concentration of from about 0.1% w/w to about 15% by weight, such as, e.g., from about from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Vitamins and Minerals

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine. In some embodiments, the active ingredient comprises one or more of vitamin B6 and B12. In some embodiments, the active ingredient comprises theanine and one or more of vitamin B6 and B12.

When present, a vitamin or combination of vitamins (e.g., vitamin B6, vitamin B12, vitamin E, vitamin C, or a combination thereof) is typically at a concentration of from about 0.01% w/w to about 1% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, or about 1% by weight, based on the total weight of the composition.

In some embodiments, the active ingredient comprises vitamin A. In some embodiments, the vitamin A is encapsulated. In some embodiments, the vitamin is vitamin B6, vitamin B12, vitamin E, vitamin C, or a combination thereof.

In some embodiments, the active ingredient comprises a mineral. As used herein, the term "mineral" refers to an inorganic molecule (or related set of molecules) that is an essential micronutrient needed for the proper functioning of various systems in a mammal. Non-limiting examples of minerals include iron, zinc, copper, selenium, chromium, cobalt, manganese, calcium, phosphorus, sulfur, magnesium, and the like. In some embodiments, the active ingredient comprises iron. Suitable sources of iron include, but are not limited to, ferrous salts such as ferrous sulfate and ferrous gluconate. In some embodiments, the iron is encapsulated.

Cannabinoids

In some embodiments, the active ingredient comprises one or more cannabinoids. As used herein, the term "cannabinoid" refers to a class of diverse natural or synthetic chemical compounds that acts on cannabinoid receptors (i.e., CB1 and CB2) in cells that alter neurotransmitter release in the brain. Cannabinoids are cyclic molecules exhibiting particular properties such as the ability to easily cross the blood-brain barrier. Cannabinoids may be naturally occurring (Phytocannabinoids) from plants such as *Cannabis*, (endocannabinoids) from animals, or artificially manufactured (synthetic cannabinoids). *Cannabis* species express at least 85 different phytocannabinoids, and these may be divided into subclasses, including cannabigerols, cannabichromenes, cannabidiols, tetrahydrocannabinols, cannabinols and cannabinodiols, and other cannabinoids, such as cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabmolic acid (THCA), and tetrahydrocannabivarinic acid (THCV A).

In some embodiments, the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabinolic acid (THCA), tetrahydrocannabivarinic acid (THCV A), and mixtures thereof. In some embodiments, the cannabinoid comprises at least tetrahydrocannabinol (THC). In some embodiments, the cannabinoid is tetrahydrocannabinol (THC). In some embodiments, the cannabinoid comprises at least cannabidiol (CBD). In some embodiments, the cannabinoid is cannabidiol (CBD). In some embodiments, the CBD is synthetic CBD.

In some embodiments, the cannabinoid (e.g., CBD) is added to the composition in the form of an isolate. An isolate is an extract from a plant, such as *Cannabis*, where the active material of interest (in this case the cannabinoid, such as CBD) is present in a high degree of purity, for example greater than 95%, greater than 96%, greater than 97%, greater than 98%, or around 99% purity.

In some embodiments, the cannabinoid is an isolate of CBD in a high degree of purity, and the amount of any other cannabinoid in the composition is no greater than about 1% by weight of the composition, such as no greater than about 0.5% by weight of the composition, such as no greater than about 0.1% by weight of the composition, such as no greater than about 0.01% by weight of the composition.

The choice of cannabinoid and the particular percentages thereof which may be present within the disclosed composition will vary depending upon the desired flavor, texture, and other characteristics of the composition.

In some embodiments, the cannabinoid (such as CBD) is present in the composition in a concentration of at least about 0.001% by weight of the composition, such as in a range from about 0.001% to about 2% by weight of the composition. In some embodiments, the cannabinoid (such as CBD) is present in the composition in a concentration of from about 0.1% to about 1.5% by weight, based on the total weight of the composition. In some embodiments, the cannabinoid (such as CBD) is present in a concentration from about 0.4% to about 1.5% by weight, based on the total weight of the oral composition.

Alternatively, or in addition to the cannabinoid, the active ingredient may include a cannabimimetic, which is a class of compounds derived from plants other than *Cannabis* that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids. Such compounds can be used in the same amounts and ratios noted herein for cannabinoids.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

In some embodiments, the terpene is a terpene derivable from a phytocannabinoid producing plant, such as a plant from the stain of the *Cannabis sativa* species, such as hemp. Suitable terpenes in this regard include so-called "C10" terpenes, which are those terpenes comprising 10 carbon atoms, and so-called "C15" terpenes, which are those terpenes comprising 15 carbon atoms. In some embodiments, the active ingredient comprises more than one terpene. For example, the active ingredient may comprise one, two, three, four, five, six, seven, eight, nine, ten or more terpenes as defined herein. In some embodiments, the terpene is selected from pinene (alpha and beta), geraniol, linalool, limonene, carvone, eucalyptol, menthone, iso-menthone, piperitone, myrcene, beta-bourbonene, germacrene and mixtures thereof.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, *Uva ursi*, valerian, wild yam root, wintergreen, yacon root, yellow dock, yerba mate, yerba santa, *Bacopa monniera, Withania somnifera*, Lion's mane, and *Silybum marianum*. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids.

Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient is a combination of citicoline, caffeine, theanine, and ginseng. In some embodiments, the active ingredient comprises sunflower lecithin. In some embodiments, the active ingredient is a combination of sunflower lecithin, caffeine, theanine, and ginseng.

The amount of API may vary. For example, when present, an API is typically at a concentration of from about 0.001% w/w to about 10% by weight, such as, e.g., from about from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the composition.

Bleached Active Ingredient

In some embodiments, the composition comprises an active ingredient as disclosed herein, wherein the active ingredient is characterized as bleached. Such a bleached active ingredient may be desirable e.g., to prevent tooth discoloration during use of the composition, or so that any residue remaining in the mouth of the user after use of the product is less visible, and is less likely to cause staining of fibrous materials, such as clothing, that may contact the residue. By "bleached" active ingredient is meant an active ingredient (e.g., a botanical material or derivative thereof), which, in its natural state possesses a color, and which has been treated to reduce or eliminate the color. By "color" is meant the characteristic of human visual perception described through color categories, with names such as red, blue, yellow (primary colors) or brown, orange, green, purple, and the like, resulting from combinations of primary colors. This perception of color derives from the stimulation of cone cells in the human eye by electromagnetic radiation in the visible spectrum, associated with objects through the wavelength of the light that is reflected from them. This reflection is governed by the object's physical properties such as e.g., absorption and emission spectra across the electromagnetic spectrum.

Certain active ingredients, by virtue of naturally occurring chemical compounds therein which reflect light in the visible range of the electromagnetic spectrum, impart a color to the active ingredient (e.g., chlorophyll or pigment decomposition products in certain botanical materials, responsible for green color and brown colors, respectively). Such chemical compounds, or a portion thereof, which are responsible for the color of the active ingredient, may be chemically altered or removed by various treatments. In some embodiments, the treatment is effective to eliminate at least 70% of the chemicals present in the active ingredient having maximum transmission of wavelengths in the visible range of the electromagnetic spectrum, based on the weight of the naturally occurring compounds. For example, such treatment may be effective to remove 70%, 80%, 90%, 95%, 99%, or even 100% of the naturally occurring compounds responsible for the visible color of the active ingredient.

In some embodiments, the treatment for bleaching (i.e., altering or removing colored chemical compounds from the active ingredient) includes extraction, chemical bleaching, or a combination thereof. One particularly suitable extraction method is supercritical carbon dioxide ($CO_2$) extraction. Methods of chemical bleaching of e.g., botanical materials, including tobacco, are known, and include as non-limiting examples, treatment with hydrogen peroxide, ozone, or other oxidizing agents. For example, bleached active ingredients (e.g., a bleached botanical or tobacco material) may be produced by various whitening methods using various bleaching or oxidizing agents. Example oxidizing agents include peroxides (e.g., hydrogen peroxide), chlorite salts, chlorate salts, perchlorate salts, hypochlorite salts, ozone, ammonia, potassium permanganate, and combinations thereof. Oxidation catalysts can be used. Example oxidation catalysts are titanium dioxide, manganese dioxide, and combinations thereof.

Methods of bleaching known for bleaching tobacco may be applied to the present active ingredients. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat.

No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the bleached active agent, or the composition or product comprising the bleached active agent, can have an ISO brightness of at least about 50%, at least about 60%, at least about 65%, at least about 70%, at least about 75%, or at least about 80%. In some embodiments, the bleached active agent or the composition or product comprising the bleached active agent, can have an ISO brightness in the range of about 50% to about 90%, about 55% to about 75%, or about 60% to about 70%. ISO brightness can be measured according to ISO 3688:1999 or ISO 2470-1:2016.

In some embodiments, the bleached active agent can be characterized as lightened in color (e.g., "whitened") in comparison to an untreated active agent. White colors are often defined with reference to the International Commission on Illumination's (CIE's) chromaticity diagram. The bleached active agent or the composition or product comprising the bleached active agent, can, in certain embodiments, be characterized as closer on the chromaticity diagram to pure white than an untreated active agent or composition or product comprising an untreated active agent.

Whiteness values of bleached active ingredients, compositions, and pouched products comprising such ingredients, may be determined according to the Commission Internationale de l'Eclairage (CIE) model, for example, with a hand-held color meter, relative to a control product (See "Precise Color Communication; Color Control from Perception to Instrumentation," Konica Minolta, 2007; http://konicaminolta.com/instruments/about/network, which is incorporated herein by reference). Discoloration from white may be evaluated by the E313 Whiteness Index according to ASTM method E313, using the formula WI=(3.388Z-3Y, where Y and Z are the CIE tri-stimulus values, and measured by a hand-held meter.

Encapsulation and Stabilization of Active Ingredients

In some embodiments, the active ingredient as described herein may be sensitive to degradation (e.g., oxidative, photolytic, thermal, evaporative) during processing or upon storage of the composition. In such embodiments, the active ingredient (such as caffeine, vitamin A, and iron (Fe)) may be encapsulated, or the composition otherwise modified with suitable components (such as fillers, binders, and the like), to provide enhanced stability to the active ingredient. For example, binders such as functional celluloses (e.g., cellulose ethers including, but not limited to, hydroxypropyl cellulose) or alginate-based materials (e.g., cross linked alginate) may be employed to enhance stability of such actives toward degradation, or to provide extended and/or separate delivery of active ingredients. Additionally, encapsulated actives may need to be paired with an excipient in the composition to increase their solubility and/or bioavailability. Non-limiting examples of suitable excipients include beta-carotene, lycopene, Vitamin D, Vitamin E, Co-enzyme Q10, Vitamin K, and curcumin.

In other embodiments, in order to provide a desired concentration of the active ingredient by weight, an initial quantity of the active ingredient may be increased to compensate for a gradual degradative loss. Accordingly, larger initial amounts than those disclosed herein are contemplated by the present disclosure.

Ion Pairing of Basic Amine-Containing Active Ingredients and Organic Acids

In some embodiments, the oral composition as disclosed herein comprises an active ingredient having a basic amine functionality (i.e., the active ingredient comprises a basic amine). By "basic amine" is meant a molecule including at least one basic amine functional group. Examples of basic amines include, but are not limited to, alkaloids. By "basic amine functional group" is meant a group containing a nitrogen atom having a lone pair of electrons. The basic amine functional group is attached to or incorporated within the molecule through one or more covalent bonds to the said nitrogen atom. The basic amine may be a primary, secondary, or tertiary amine, meaning the nitrogen bears one, two, or three covalent bonds to carbon atoms. By virtue of the lone pair of electrons on the nitrogen atom, such amines are termed "basic", meaning the lone electron pair is available for hydrogen bonding. The basicity (i.e., the electron density on the nitrogen atom and consequently the availability and strength of hydrogen bonding to the nitrogen atom) of the basic amine may be influenced by the nature of neighboring atoms, the steric bulk of the molecule, and the like.

Generally, the basic amine is released from the composition and absorbed through the oral mucosa, thereby entering the blood stream, where it is circulated systemically. Generally, the basic amine is present in or as an active ingredient in the composition, as described herein below.

In some embodiments, the active ingredient having the basic amine functionality is caffeine. In some embodiments, the active ingredient having a basic amine functionality is nicotine, for example, a nicotine component as described herein above.

In some embodiments, at least a portion the active ingredient having the basic amine functionality (e.g., nicotine) is associated with at least a portion of the organic acid or the alkali metal salt thereof. Depending on multiple variables (concentration, pH, nature of the organic acid, and the like), the active ingredient having the basic amine functionality present in the composition can exist in multiple forms, including ion paired, in solution (i.e., fully solvated), as the free base, as a cation, as a salt, or any combination thereof.

In some embodiments, at least a portion of the active ingredient present in the composition and having the basic amine functionality is in an ion paired form with the organic acid or conjugate base thereof as further described herein below. In some embodiments, the active ingredient having the basic amine functionality and at least a portion of the organic acid or the alkali metal salt thereof is in the form of an ion pair between the basic amine and a conjugate base of the organic acid.

Ion pairing describes the partial association of oppositely charged ions in relatively concentrated solutions to form distinct chemical species called ion pairs. The strength of the association (i.e., the ion pairing) depends on the electrostatic force of attraction between the positive and negative ions (i.e., a protonated basic amine and the conjugate base of an organic acid). By "conjugate base" is meant the base resulting from deprotonation of the corresponding acid (e.g., benzoate is the conjugate base of benzoic acid).

On average, a certain population of these ion pairs exists at any given time, although the formation and dissociation of ion pairs is continuous. In the composition as disclosed herein, and/or upon oral use of said composition (e.g., upon contact with saliva), the active ingredient having the basic amine functionality and the conjugate base of the organic acid exist at least partially in the form of an ion pair. Without wishing to be bound by theory, it is believed that such ion pairing may minimize chemical degradation of the active ingredient having the basic amine functionality and/or enhance the oral availability of the active ingredient having the basic amine functionality. At alkaline pH values (e.g., such as from about 7.5 to about 9), certain active ingredient having the basic amine functionality, for example nicotine, are largely present in the free base form, which has relatively low water solubility, and low stability with respect to evaporation and oxidative decomposition, but high mucosal availability. Conversely, at acidic pH values (such as from about 6.5 to about 4), certain active ingredient having the basic amine functionality, for example nicotine, are largely present in a protonated form, which has relatively high water solubility, and higher stability with respect to evaporation and oxidative decomposition, but low mucosal availability. In some embodiments, the properties of stability, solubility, and availability of nicotine can be enhanced through ion pairing or salt formation of nicotine with appropriate organic acids and/or their conjugate bases. Specifically, nicotine-organic acid ion pairs of moderate lipophilicity result in favorable stability and absorption properties. Lipophilicity is conveniently measured in terms of log P, the partition coefficient of a molecule between a lipophilic phase and an aqueous phase, usually octanol and water, respectively. An octanol-water partitioning favoring distribution of an ion pair into octanol is predictive of good absorption of the active ingredient having the basic amine functionality present in the composition through the oral mucosa.

As noted above, at alkaline pH values (e.g., such as from about 7.5 to about 9), nicotine is largely present in the free base form (and accordingly, a high partitioning into octanol), while, at acidic pH values (such as from about 6.5 to about 4), nicotine is largely present in a protonated form (and accordingly, a low partitioning into octanol). Surprisingly, according to the present disclosure, it has been found that an ion pair between certain organic acids (e.g., having a log P value of from about 1.4 to about 8.0. such as from about 1.4 to about 4.5, allows nicotine partitioning into octanol consistent with that predicted for nicotine partitioning into octanol at a pH of 8.4.

One of skill in the art will recognize that the extent of ion pairing in the disclosed composition, both before and during use by the consumer, may vary based on, for example, pH, the nature of the organic acid, the concentration of nicotine, the concentration of the organic acid or conjugate base of the organic acid present in the composition, the moisture content of the composition, the ionic strength of the composition, and the like. One of skill in the art will also recognize that ion pairing is an equilibrium process influenced by the foregoing variables. Accordingly, quantification of the extent of ion pairing is difficult or impossible by calculation or direct observation. However, the presence of ion pairing may be demonstrated through surrogate measures such as partitioning between octanol and water or membrane permeation of aqueous solutions of nicotine plus organic acids and/or their conjugate bases.

Organic Acid

As discussed herein above, in some embodiments, the oral composition as disclosed herein comprises an organic acid, an alkali metal salt thereof, or both. In some embodiments, at least a portion of the organic acid or salt thereof is in the form of an ion pair with a basic amine-containing active ingredient as described herein above.

As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($—CO_2H$) or sulfonic acids ($—SO_2OH$). As used herein, reference to organic acid means an organic acid that is intentionally added. In this regard, an organic acid may be intentionally added as a specific composition ingredient as opposed to merely being inherently present as a component of another composition ingredient (e.g., the small amount of organic acid which may inherently be present in a composition ingredient, such as a tobacco material).

Suitable organic acids will typically have a range of lipophilicities (i.e., a polarity giving an appropriate balance of water and organic solubility). Typically, lipophilicities of suitable organic acids, as indicated by log P, will vary between about 1 and about 12 (more soluble in octanol than in water). In some embodiments, the organic acid has a log P value from about 1 to about 12, e.g., from about 1.0. about 1.5, about 2.0, about 2.5, about 3.0, about 3.5, about 4.0, about 4.5, about 5.0, about 5.5, about 6.0, about 6.5, about 7.0, about 7.5, or about 8.0, to about 8.5, about 9.0, about 9.5, about 10.0, about 10.5, about 11.0, about 11.5, or about 12.0.

Without wishing to be bound by theory, it is believed that moderately lipophilic organic acids (e.g., log P of from about 1.4 to about 4.5) produce ion pairs with nicotine which are of a polarity providing good octanol-water partitioning of the ion pair, and hence partitioning of nicotine, into octanol versus water. As discussed above, such partitioning into octanol is predictive of favorable oral availability.

In specific embodiments, the organic acid has a log P value from about 3.0 to about 8.0, about 10.0, or even 12.0. In some embodiments, the presence of certain solvents or solubilizing agents (e.g., inclusion in the composition of glycerin or propylene glycol) may be beneficial in solubilizing organic acids and the corresponding salts or ion pairs thereof with the basic amine for highly lipophilic organic acids (e.g., higher than about 4.5).

In some embodiments, the organic acid is a carboxylic acid or a sulfonic acid. The carboxylic acid or sulfonic acid functional group may be attached to any alkyl, cycloalkyl, heterocycloalkyl, aryl, or heteroaryl group having, for example, from one to twenty carbon atoms ($C_1$-$C_{20}$). In some embodiments, the organic acid is an alkyl, cycloalkyl, heterocycloalkyl, aryl, or heteroaryl carboxylic or sulfonic acid.

As used herein, "alkyl" refers to any straight chain or branched chain hydrocarbon. The alkyl group may be saturated (i.e., having all $sp^3$ carbon atoms), or may be unsaturated (i.e., having at least one site of unsaturation). As used herein, the term "unsaturated" refers to the presence of a carbon-carbon, $sp^2$ double bond in one or more positions within the alkyl group. Unsaturated alkyl groups may be mono- or polyunsaturated. Representative straight chain alkyl groups include, but are not limited to, methyl, ethyl, n-propyl, n-butyl, n-pentyl, and n-hexyl. Branched chain alkyl groups include, but are not limited to, isopropyl, sec-butyl, isobutyl, tert-butyl, isopentyl, and 2-methylbutyl. Representative unsaturated alkyl groups include, but are not limited to, ethylene or vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like. An alkyl group can be unsubstituted or substituted.

"Cycloalkyl" as used herein refers to a carbocyclic group, which may be mono- or bicyclic. Cycloalkyl groups include rings having 3 to 7 carbon atoms as a monocycle or 7 to 12 carbon atoms as a bicycle. Examples of monocyclic cycloalkyl groups include cyclopropyl, cyclobutyl, cyclopentyl, cyclohexyl, cycloheptyl, and cyclooctyl. A cycloalkyl group can be unsubstituted or substituted, and may include one or more sites of unsaturation (e.g., cyclopentenyl or cyclohexenyl).

The term "aryl" as used herein refers to a carbocyclic aromatic group. Examples of aryl groups include, but are not limited to, phenyl and naphthyl. An aryl group can be unsubstituted or substituted.

"Heteroaryl" and "heterocycloalkyl" as used herein refer to an aromatic or non-aromatic ring system, respectively, in which one or more ring atoms is a heteroatom, e.g. nitrogen, oxygen, and sulfur. The heteroaryl or heterocycloalkyl group comprises up to 20 carbon atoms and from 1 to 3 heteroatoms selected from N, O, and S. A heteroaryl or heterocycloalkyl may be a monocycle having 3 to 7 ring members (for example, 2 to 6 carbon atoms and 1 to 3 heteroatoms selected from N, O, and S) or a bicycle having 7 to 10 ring members (for example, 4 to 9 carbon atoms and 1 to 3 heteroatoms selected from N, O, and S), for example: a bicyclo[4,5], [5,5], [5,6], or [6,6] system. Examples of heteroaryl groups include by way of example and not limitation, pyridyl, thiazolyl, tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, benzotriazolyl, benzisoxazolyl, and isatinoyl. Examples of heterocycloalkyls include by way of example and not limitation, dihydroypyridyl, tetrahydropyridyl (piperidyl), tetrahydrothiophenyl, piperidinyl, 4-piperidonyl, pyrrolidinyl, 2-pyrrolidonyl, tetrahydrofuranyl, tetrahydropyranyl, bis-tetrahydropyranyl, tetrahydroquinolinyl, tetrahydroisoquinolinyl, decahydroquinolinyl, octahydroisoquinolinyl, piperazinyl, quinuclidinyl, and morpholinyl. Heteroaryl and heterocycloalkyl groups can be unsubstituted or substituted.

"Substituted" as used herein and as applied to any of the above alkyl, aryl, cycloalkyl, heteroaryl, heterocyclyl, means that one or more hydrogen atoms are each independently replaced with a substituent. Typical substituents include, but are not limited to, —Cl, Br, F, alkyl, —OH, —$OCH_3$, $NH_2$, —$NHCH_3$, —$N(CH_3)_2$, —CN, —NC(=O)$CH_3$, —C(=O)—, —C(=O)$NH_2$, and —C(=O)$N(CH_3)_2$. Wherever a group is described as "optionally substituted," that group can be substituted with one or more of the above substituents, independently selected for each occasion. In some embodiments, the substituent may be one or more methyl groups or one or more hydroxyl groups.

In some embodiments, the organic acid is an alkyl carboxylic acid. Non-limiting examples of alkyl carboxylic acids include formic acid, acetic acid, propionic acid, butyric acid, valeric acid, caproic acid, heptanoic acid, octanoic acid, nonanoic acid, decanoic acid, undecanoic acid, dodecanoic acid, stearic acid, oleic acid, linoleic acid, linolenic acid, and the like.

In some embodiments, the organic acid is an alkyl sulfonic acid. Non-limiting examples of alkyl sulfonic acids include propanesulfonic acid, heptanesulfonic acid, and octanesulfonic acid.

In some embodiments, the alkyl carboxylic or sulfonic acid is substituted with one or more hydroxyl groups. Non-limiting examples include glycolic acid, 4-hydroxybutyric acid, and lactic acid.

In some embodiments, an organic acid may include more than one carboxylic acid group or more than one sulfonic acid group (e.g., two, three, or more carboxylic acid groups). Non-limiting examples include oxalic acid, fumaric acid, maleic acid, and glutaric acid. In organic acids containing multiple carboxylic acids (e.g., from two to four carboxylic acid groups), one or more of the carboxylic acid groups may be esterified. Non-limiting examples include succinic acid monoethyl ester, monomethyl fumarate, monomethyl or dimethyl citrate, and the like.

In some embodiments, the organic acid may include more than one carboxylic acid group and one or more hydroxyl groups. Non-limiting examples of such acids include tartaric acid, citric acid, and the like.

In some embodiments, the organic acid is an aryl carboxylic acid or an aryl sulfonic acid. Non-limiting examples of aryl carboxylic and sulfonic acids include benzoic acid, toluic acids, salicylic acid, benzenesulfonic acid, and p-toluenesulfonic acid.

Further non-limiting examples of organic acids which may be useful in certain embodiments include 2,2-dichloroacetic acid, 2-hydroxyethanesulfonic acid, 2-oxoglutaric acid, 4-acetamidobenzoic acid, 4-aminosalicylic acid, adipic acid, ascorbic acid (L), aspartic acid (L), alpha-methylbutyric acid, camphoric acid (+), camphor-10-sulfonic acid (+), cinnamic acid, cyclamic acid, dodecylsulfuric acid, ethane-1,2-disulfonic acid, ethanesulfonic acid, furoic acid, galactaric acid, gentisic acid, glucoheptonic acid, gluconic acid, glucuronic acid, glutamic acid, glycerophosphoric acid, glycolic acid, hippuric acid, isobutyric acid, isovaleric acid, lactobionic acid, lauric acid, levulinic acid, malic acid, malonic acid, mandelic acid, methanesulfonic acid, naphthalene-1,5-disulfonic acid, naphthalene-2-sulfonic acid, oleic acid, palmitic acid, pamoic acid, phenylacetic acid, pyroglutamic acid, pyruvic acid, sebacic acid, stearic acid, and undecylenic acid. Examples of suitable acids include, but are not limited to, the list of organic acids in Table 1.

TABLE 1

Non-limiting examples of suitable organic acids

| Acid Name | log(P)* |
|---|---|
| benzoic acid | 1.9 |
| phenylacetic | 1.4 |
| p-toluic acid | 2.3 |
| ethyl benzoic acid | 2.9 |
| isopropyl benzoic acid | 3.5 |
| 4-phenylbutyric | 2.4 |
| 2-(4-Isobutylphenyl)propanoic acid | 3.5 |
| 2-napthoxyacetic acid | 2.5 |
| napthylacetic acid | 2.7 |
| heptanoic acid | 2.5 |
| octanoic acid | 3.05 |
| nonanoic acid | 3.5 |
| decanoic acid | 4.09 |
| 9-deceneoic acid | 3.3 |
| 2-deceneoic acid | 3.8 |
| 10-undecenoic acid | 3.9 |
| dodecandioic acid | 3.2 |
| dodecanoic acid | 4.6 |
| myristic acid | 5.3 |
| palmitic acid | 6.4 |
| stearic acid | 7.6 |
| cyclohexanebutanoic acid | 3.4 |
| 1-heptanesulfonic acid | 2.0 |

TABLE 1-continued

Non-limiting examples of suitable organic acids

| Acid Name | log(P)* |
|---|---|
| 1-octanesulfonic acid | 2.5 |
| 1-nonanesulfonic acid | 3.1 |
| monooctyl succinate | 2.8 |
| tocopherol succinate | 10.2 |
| monomenthyl succinate | 3 |
| monomenthyl glutarate | 3.4 |
| norbixin ((2E,4E,6E,8E,10E,12E,14E,16E,18E)-4,8,13,17-tetramethylicosa-2,4,6,8,10,12,14,16,18-nonaenedioic acid) | 7.2 |
| bixin ((2E,4E,6E,8E,10E,12E,14E,16Z,18E)-20-methoxy-4,8,13,17-tetramethyl-20-oxoicosa-2,4,6,8,10,12,14,16,18-nonaenoic acid) | 7.5 |

*Values obtained from PubChem or calculated

The selection of organic acid may further depend on additional properties in addition to consideration of the log P value. For example, an organic acid should be one recognized as safe for human consumption, and which has acceptable flavor, odor, volatility, stability, and the like. Determination of appropriate organic acids is within the purview of one of skill in the art.

In some embodiments, the organic acid is a mono ester of a dicarboxylic acid or a poly-carboxylic acid. In some embodiments, the dicarboxylic acid is malonic acid, succinic acid, glutaric acid, adipic acid, fumaric acid, maleic acid, or a combination thereof. In some embodiments, the dicarboxylic acid is succinic acid, glutaric acid, fumaric acid, maleic acid, or a combination thereof. In some embodiments, the dicarboxylic acid is succinic acid, glutaric acid, or a combination thereof.

In some embodiments, the alcohol forming the mono ester of the dicarboxylic acid is a lipophilic alcohol. Examples of suitable lipophilic alcohols include, but are not limited to, octanol, menthol, and tocopherol. In some embodiments, the organic acid is an octyl mono ester of a dicarboxylic acid, such as monooctyl succinate, monooctyl fumarate, or the like. In some embodiments, the organic acid is a monomenthyl ester of a dicarboxylic acid. Certain menthyl esters may be desirable in oral compositions as described herein by virtue of the cooling sensation they may provide upon use of the product comprising the composition. In some embodiments, the organic acid is monomenthyl succinate, monomenthyl fumarate, monomenthyl glutarate, or a combination thereof. In some embodiments, the organic acid is a monotocopheryl ester of a dicarboxylic acid. Certain tocopheryl esters may be desirable in oral compositions as described herein by virtue of the antioxidant effects they may provide. In some embodiments, the organic acid is tocopheryl succinate, tocopheryl fumarate, tocopheryl glutarate, or a combination thereof.

In some embodiments, the organic acid is a carotenoid derivative having one or more carboxylic acids. Carotenoids are tetraterpenes, meaning that they are produced from 8 isoprene molecules and contain 40 carbon atoms. Accordingly, they are usually lipophilic due to the presence of long unsaturated aliphatic chains, and are generally yellow, orange, or red in color. Certain carotenoid derivatives can be advantageous in oral compositions by virtue of providing both ion pairing and serving as a colorant in the composition. In some embodiments, the organic acid is 2E,4E,6E,8E,10E,12E,14E,16Z,18E)-20-methoxy-4,8,13,17-tetramethyl-20-oxoicosa-2,4,6,8,10,12,14,16,18-nonaenoic acid (bixin) or an isomer thereof. Bixin is an apocarotenoid found in annatto seeds from the achiote tree (*Bixa orellana*) and is the naturally occurring pigment providing the reddish orange color to annatto. Bixin is soluble in fats and alcohols but insoluble in water, and is chemically unstable when isolated, converting via isomerization into the double bond isomer, trans-bixin (β-bixin), having the structure:

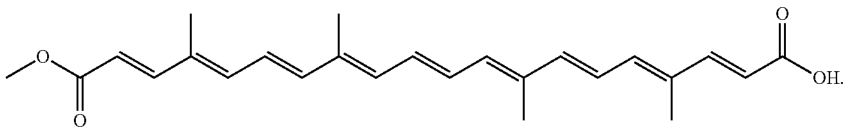 [SMILES: COC(=O)/C=C/C(C)=C/C=C/C(C)=C/C=C/C=C(C)/C=C/C=C(C)/C=C/C(=O)O]

In some embodiments, the organic acid is (2E,4E,6E,8E,10E,12E,14E,16E,18E)-4,8,13,17-tetramethylicosa-2,4,6,8,10,12,14,16,18-nonaenedioic acid (norbixin), a water-soluble hydrolysis product of bixin having the structure:

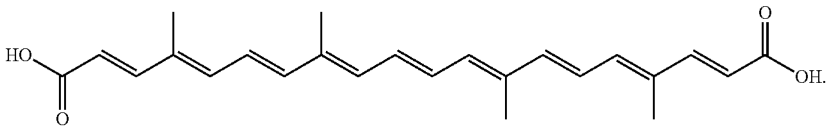 [SMILES: CC(/C=C/C=C(C)/C=C/C(=O)O)=C\C=C\C=C(C)\C=C\C=C(C)\C=C\C(=O)O]

The selection of organic acid may further depend on additional properties in addition to or without consideration to the log P value. For example, an organic acid should be one recognized as safe for human consumption, and which has acceptable flavor, odor, volatility, stability, and the like. Determination of appropriate organic acids is within the purview of one of skill in the art.

In some embodiments, more than one organic acid may be present. For example, the composition may comprise two, or three, or four, or more organic acids. Accordingly, reference herein to "an organic acid" contemplates mixtures of two or more organic acids. The relative amounts of the multiple organic acids may vary. For example, a composition may comprise equal amounts of two, or three, or more organic acids, or may comprise different relative amounts. In this manner, it is possible to include certain organic acids (e.g., citric acid or myristic acid) which have a log P value outside the desired range, when combined with other organic acids to provide the desired average log P range for the combination. In some embodiments, it may be desirable to include organic acids in the composition which have log P values outside the desired range for purposes such as, but not limited to, providing desirable organoleptic properties, stability, as flavor components, and the like. Further, certain lipophilic organic acids have undesirable flavor and or aroma characteristics which would preclude their presence as the sole organic acid (e.g., in equimolar or greater quantities relative to nicotine). Without wishing to be bound by theory, it is believed that a combination of different organic acids may provide the desired ion pairing while the concentration of any single organic acid in the composition remains below the threshold which would be found objectionable from a sensory perspective.

For example, in some embodiments, the organic acid may comprise from about 1 to about 5 or more molar equivalents of benzoic acid relative to nicotine, combined with e.g., about 0.2 molar equivalents of octanoic acid or a salt thereof, and 0.2 molar equivalents of decanoic acid or a salt thereof.

In some embodiments, the organic acid is a combination of any two organic acids selected from the group consisting of benzoic acid, a toluic acid, benzenesulfonic acid, toluenesulfonic acid, hexanoic acid, heptanoic acid, decanoic acid, and octanoic acid. In some embodiments, the organic acid is a combination of benzoic acid, octanoic acid, and decanoic acid, or benzoic and octanoic acid. In some embodiments, the composition comprises citric acid in addition to one or more of benzoic acid, a toluic acid, benzenesulfonic acid, toluenesulfonic acid, hexanoic acid, heptanoic acid, decanoic acid, and octanoic acid.

In some embodiments, the oral composition comprises an alkali metal salt of an organic acid. For example, at least a portion of the organic acid may be present in the composition in the form of an alkali metal salt. Suitable alkali metal salts include lithium, sodium, and potassium. In some embodiments, the alkali metal is sodium or potassium. In some embodiments, the alkali metal is sodium. In some embodiments, the composition comprises an organic acid and a sodium salt of the organic acid.

In some embodiments, the oral composition comprises benzoic acid and sodium benzoate, octanoic acid and sodium octanoate, decanoic acid and sodium decanoate, or a combination thereof. In some embodiments, the composition comprises benzoic acid and sodium benzoate. In some embodiments, the composition comprises sodium benzoate.

In some embodiments, the ratio of the organic acid to the sodium salt (or other alkali metal salt) of the organic acid is from about 0.1 to about 10, such as from about 0.1, about 0.25, about 0.3, about 0.5, about 0.75, or about 1, to about 2, about 5, or about 10. For example, in some embodiments, both an organic acid and the sodium salt thereof are added to the other components of the composition, wherein the organic acid is added in excess of the sodium salt, in equimolar quantities with the sodium salt, or as a fraction of the sodium salt. One of skill in the art will recognize that the relative amounts will be determined by the desired pH of the composition, as well as the desired ionic strength. For example, the organic acid may be added in a quantity to provide a desired pH level of the composition, while the alkali metal (e.g., sodium) salt is added in a quantity to provide the desired extent of ion pairing. As one of skill in the art will understand, the quantity of organic acid (i.e., the protonated form) present in the composition, relative to the alkali metal salt or conjugate base form present in the composition, will vary according to the pH of the composition and the pKa of the organic acid, as well as according to the actual relative quantities initially added to the composition.

The amount of organic acid or an alkali metal salt thereof present in the oral composition, relative to the basic amine containing active ingredient (e.g., nicotine), may vary. Generally, as the concentration of the organic acid (or the conjugate base thereof) increases, the percent of nicotine that is ion paired with the organic acid increases. This typically increases the partitioning of the nicotine, in the form of an ion pair, into octanol versus water as measured by the log P (the $\log_{10}$ of the partitioning coefficient). In some embodiments, the composition comprises from about 0.05, about 0.1, about 1, about 1.5, about 2, or about 5, to about 10, about 15, or about 20 molar equivalents of the organic acid, the alkali metal salt thereof, or the combination thereof, relative to the nicotine component, calculated as free base nicotine.

In some embodiments, the oral composition comprises from about 2 to about 10, or from about 2 to about 5 molar equivalents of the organic acid, the alkali metal salt thereof, or the combination thereof, to nicotine, on a free-base nicotine basis. In some embodiments, the organic acid, the alkali metal salt thereof, or the combination thereof, is present in a molar ratio with the nicotine from about 2, about 3, about 4, or about 5, to about 6, about 7, about 8, about 9, or about 10. In embodiments wherein more than one organic acid, alkali metal salt thereof, or both, are present, it is to be understood that such molar ratios reflect the totality of the organic acids present.

In certain embodiments the organic acid inclusion is sufficient to provide a pH of the oral composition from about 4.0 to about 9.5, such as from about 4.0 to about 9.0, or from about 4.0 to about 8.5, or from about 4.0 to about 8.0, or from about 4.5 to about 7.5, or from about 4.5 to about 7.0, or from about 5.5 to about 7.0, or from about 4.0 to about 5.5, or from about 7.0 to about 9.5. In some embodiments, the organic acid inclusion is sufficient to provide a composition pH of about 4.0, about 4.5, about 5.0, about 5.5, about 6.0, about 6.5, about 7.0, about 7.5, about 8.0, about 8.5, or about 9.0. In some embodiments, the organic acid inclusion is sufficient to provide a composition pH of from about 4.5 to about 6.5, for example, from about 4.5, about 5.0, or about 5.5, to about 6.0, or about 6.5. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5. In other embodiments, a mineral acid (e.g., hydrochloric acid, sulfuric acid, phosphoric acid, or the like) is added to adjust the pH of the composition to the desired value.

In some embodiments, the organic acid is added as the free acid, either neat (i.e., native solid or liquid form) or as a solution in, e.g., water, to the other oral composition components. In some embodiments, the alkali metal salt of the organic acid is added, either neat or as a solution in, e.g., water, to the other oral composition components.

In some embodiments, the organic acid is added as the free acid, either neat (i.e., native solid or liquid form) or as a solution in, e.g., water, to the other composition components. In some embodiments, the alkali metal salt of the organic acid is added, either neat or as a solution in, e.g., water, to the other composition components. In some embodiments, the organic acid and the basic amine (e.g., nicotine) are combined to form a salt, either before addition to the composition, or the salt is formed within and is present in the composition as such. In other embodiments, the organic acid and basic amine (e.g., nicotine) are present as individual components in the composition, and form an ion pair upon contact with moisture (e.g., saliva in the mouth of the consumer).

In some embodiments, the oral composition comprises nicotine benzoate and sodium benzoate, wherein at least a portion of the nicotine and benzoate ions present are in an ion paired form. In some embodiments, the composition comprises nicotine benzoate, sodium benzoate, and an organic acid, an alkali metal salt of an organic acid, or a combination thereof, the organic acid having a log P value from about 1 to about 12, wherein the organic acid is a monoester of a dicarboxylic acid or is a carotenoid derivative having one or more carboxylic acids.

In some embodiments, the oral composition further comprises a solubility enhancer to increase the solubility of one or more of the organic acid or salt thereof. Suitable solubility enhancers include, but are not limited to, humectants as described herein, such as glycerol or propylene glycol.

In particular embodiments, the oral composition comprises nicotine benzoate and sodium benzoate. In some embodiments, the sodium benzoate is present in a molar ratio to the nicotine benzoate in a range from about 1 to about 20, such as about 2, about 5, or about 10. In some embodiments, the oral composition further comprises nicotine polacrilex. In some embodiments, the total amount of nicotine present in the composition is provided in equal quantities from nicotine benzoate and nicotine polacrilex. In other embodiments, the oral composition includes only nicotine polacrilex as the nicotine source, and the composition optionally comprises an organic acid component such as sodium benzoate.

Flavoring Agent and Flavor Granules

In some embodiments, the oral composition comprises a flavoring agent. As used herein, a "flavoring agent" or "flavorant" is any flavorful or aromatic substance capable of altering the sensory characteristics associated with the composition. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy.

Flavoring agents may be imitation, synthetic or natural ingredients or blends thereof. Flavoring agents may include naturally occurring flavor materials, botanicals, extracts of botanicals, synthetically obtained materials, or combinations thereof (e.g., tobacco, *Cannabis*, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents.

Flavorants may further include flavor enhancers, bitterness receptor site blockers, sensorial receptor site activators or stimulators, and trigeminal sensates, As used herein, "trigeminal sensate" refers to a flavoring agent which has an effect on the trigeminal nerve, producing sensations including heating, cooling, tingling, and the like. Non-limiting examples of trigeminal sensate flavoring agents include capsaicin, citric acid, menthol, Sichuan buttons, erythritol, and cubebol. A suitable heat effect agent may be, but is not limited to, vanillyl ethyl ether, and a suitable cooling agent may be, but is not limited to eucalyptol or N-ethyl-p-menthane-3-carboxamide (WS-3).

Flavoring agents may be in any suitable form, for example, liquid such as an oil, solid such as a powder, or gas. In some instances, the flavoring agent may be provided in a spray-dried form or a liquid form. In some embodiments, a liquid flavorant is disposed (i.e., adsorbed or absorbed in or on) a porous particulate carrier, for example microcrystalline cellulose, which is then combined with the other composition ingredients.

The amount of flavoring agent utilized in the oral composition can vary, but is typically up to about 10% by weight, and certain embodiments are characterized by a flavoring agent content of at least about 0.1% by weight, such as about 0.5 to about 10%, about 1 to about 5%, or about 2 to about 4% weight, based on the total weight of the composition.

In some embodiments, the oral composition comprises flavor granules. The term "flavor granules" as used here in means that the flavoring agent(s) are encapsulated in a matrix which provide an altered release pattern of the flavoring agent, for example, delayed or sustained release of the flavoring agent(s). Such flavor granules are generally in the form of small beads or particles (e.g., in a size range of about 14 to about 20 mesh, or about 0.5 to about 1.5 mm). Without wishing to be bound by theory, it is believed that the presence of flavor granules in the oral composition provides desirable qualities to the overall composition, such as visual interest, additional textures, and/or delayed or extended delivery of flavors. Such flavors may be the same or different from other flavors present in the remainder of the composition. Suitable flavor granules typically comprise a sugar alcohol, filler, sweetener, humectant, colorant, and flavorant, or comprise a combination of two or more sugar alcohols, sweetener, colorant, and flavorant. The quantities of each component may vary depending on the desired properties of the granules and the selection of the individual components. In some embodiments, the granules comprise a sugar alcohol in an amount by weight from about 60 to about 90%, a humectant in an amount by weight from about 15 to about 30%, a filler in an amount by weight from about 0 to about 50%; a sweetener in an amount by weight from about 0.1 to about 0.5%; a flavorant in an amount by weight from about 1 to about 30%, with the remainder of the balance being a colorant. In some embodiments, the granules comprise a combination of two sugar alcohols in a total amount by weight from about 96 to about 99%; and a sweetener in an amount by weight from about 0.1 to about 0.5%, with the remainder comprising colorant and flavorant Suitable sugar alcohols include, but are not limited to, erythritol, arabitol, ribitol, isomalt, maltitol, dulcitol, iditol, mannitol, xylitol, lactitol, sorbitol, and combinations thereof. In some embodiments, the sugar alcohol is isomalt, maltitol, mannitol, xylitol, sorbitol, or a combination thereof. In some embodiments, the sugar alcohol is isomalt.

Suitable humectants include, but are not limited to, glycerin, propylene glycol, 1,3-propanediol, dipropylene glycol, and combinations thereof. In some embodiments, the humectant is glycerin.

Suitable fillers include, but are not limited to, starches (e.g., from potato, wheat, rice, corn), natural cellulose, and modified cellulosic materials. In some embodiments, the filler is a cellulose material or cellulose derivative. In some embodiments, the filler is microcrystalline cellulose ("mcc"). The mcc may be synthetic or semi-synthetic, or it may be obtained entirely from natural celluloses. The mcc may be selected from the group consisting of AVICEL© grades PH-100, PH-102, PH-103, PH-105, PH-112, PH-113, PH-200, PH-300, PH-302, VIVACEL© grades 101, 102, 12, 20 and EMOCEL© grades 50M and 90M, and the like, and mixtures thereof.

The sweetener can be any sweetener or combination of sweeteners, in natural or artificial form, or as a combination of natural and artificial sweeteners. Examples of natural sweeteners include fructose, sucrose, glucose, maltose, mannose, galactose, lactose, *stevia*, honey, and the like. Examples of artificial sweeteners include sucralose, isomaltulose, maltodextrin, saccharin, aspartame, acesulfame K, neotame, and the like. In some embodiments, the sweetener is a non-caloric artificial sweetener. In some embodiments, the sweetener is sucralose.

The flavorant and colorant are as described herein. In some embodiments, the colorant is a lake dye, such as a red or blue lake dye. As described herein above, the flavorant present in the granules may be the same or different from the flavorant present in the remainder of the composition. The components In some embodiments, the flavor granules comprise isomalt as the sugar alcohol, glycerin as the humectant, microcrystalline cellulose as the filler, and sucralose as the sweetener. In some embodiments, the flavor granules are an extruded mixture of isomalt, glycerin, sucralose, microcrystalline cellulose, colorant, and flavorant. In some embodiments, the granules consist of isomalt in an amount by weight from about 60 to about 90%, such as about 70 to about 80%; glycerin in an amount by weight from about 16 to about 22%, such as from about 18 to about 20%; microcrystalline cellulose in an amount by weight from about 1 to about 3%; sucralose in an amount by weight from about 0.1 to about 0.5%, such as about 0.2 to about 0.4%; with the balance consisting of colorant and flavorant. In some embodiments, the granules consist of isomalt in an amount by weight from about 15 to about 35%, such as about 25 to about 35%; glycerin in an amount by weight from about 15 to about 30%, such as from about 18 to about 22%; microcrystalline cellulose in an amount by weight from about 20 to about 50%, such as from about 20 to about 30%; sucralose in an amount by weight from about 0.1 to about 0.5%, such as about 0.2 to about 0.4%; and flavorant in an amount by weight from about 20 to about 30%; with the balance consisting of colorant.

In some embodiments, the flavor granules comprise isomalt and maltitol as the sugar alcohols and sucralose as the sweetener, along with flavorant and colorant. In some embodiments, the flavor granules are a melted, cooled, and crushed mixture of isomalt, maltitol syrup, sucralose, colorant, and flavorant. In some embodiments, the granules consist of isomalt in an amount by weight from about 92 to about 96%, such as about 92 to about 94%; maltitol syrup in an amount by weight from about 4 to about 6%; sucralose in an amount by weight from about 0.1 to about 0.5%, such as about 0.2 to about 0.4%; with the balance consisting of colorant and flavorant.

The quantity of flavor granules, when present in the oral composition, may vary. In some embodiments, the oral composition comprises from about 1 to about 5% by weight of flavor granules, such as from about 1, about 2, or about 3, to about 4 or about 5% flavor granules by weight, based on the total weight of the composition.

Taste Modifiers

In order to improve the organoleptic properties of an oral composition as disclosed herein, the composition may include one or more taste modifying agents ("taste modifiers") which may serve to mask, alter, block, or improve e.g., the flavor of an oral composition as described herein. Non-limiting examples of such taste modifiers include analgesic or anesthetic herbs, spices, and flavors which produce a perceived cooling (e.g., menthol, eucalyptus, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the composition comprises an active ingredient having a bitter taste, and a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., an active ingredient). In some embodiments, the taste modifier is capsaicin.

In some embodiments, the taste modifier is the amino acid gamma-amino butyric acid (GABA), referenced herein above with respect to amino acids. Studies in mice suggest that GABA may serve function(s) in taste buds in addition to synaptic inhibition. See, e.g., Dvoryanchikov et al., J Neurosci. 2011 Apr. 13; 31(15):5782-91. Without wishing to be bound by theory, GABA may suppress the perception of certain tastes, such as bitterness. In some embodiments, the composition comprises caffeine and GABA.

In some embodiments, the taste modifier is adenosine monophosphate (AMP). AMP is a naturally occurring nucleotide substance which can block bitter food flavors or enhance sweetness. It does not directly alter the bitter flavor, but may alter human perception of "bitter" by blocking the associated receptor.

In some embodiments, the taste modifier is lactisole. Lactisole is an antagonist of sweet taste receptors. Temporarily blocking sweetness receptors may accentuate e.g., savory notes.

When present, a representative amount of taste modifier is about 0.01% by weight or more, about 0.1% by weight or more, or about 1.0% by weight or more, but will typically make up less than about 10% by weight of the total weight of the oral composition, (e.g., from about 0.01%, about 0.05%, about 0.1%, or about 0.5%, to about 1%, about 5%, or about 10% by weight based on the total weight of the oral composition).

Sweetener

In order to improve the sensory and/or physical properties of the oral composition, one or more sweeteners may be added, beyond any sugar or sugar alcohol which may be present as a bulking agent. When present in the oral composition, the sweetener or mixture of sweeteners will generally be present in an amount of less than about 1% by weight of the composition, such as from about 0.1 to about 1%, or from about 0.3 to about 0.6% by weight, based on the total weight of the oral composition.

The sweetener can be any sweetener or combination of sweeteners, in natural or artificial form, or a combination of natural and artificial sweeteners. Examples of natural sweeteners include fructose, sucrose, glucose, maltose, isomaltulose, mannose, galactose, lactose, *stevia*, honey, and the like. Examples of artificial sweeteners include sucralose, maltodextrin, saccharin, aspartame, acesulfame K, neotame and the like. In some embodiments, the sweetener is an artificial sweetener. In some embodiments, the artificial sweetener is selected from the group consisting of sucralose, acesulfame K, aspartame, and mixtures thereof.

Humectant

In certain embodiments, one or more humectants may be employed in the oral composition of the present disclosure. Humectants may serve additional roles, such as softening or sweetening the oral composition. Where included, the humectant is typically provided in an amount sufficient to provide desired moisture or other physical attributes to the oral composition. When present, the humectant may be present in an amount of from about 0.01% to about 5%, such as from about 0.1 to about 3%, or from about 1 to about 2% by weight, based on the total weight of the oral composition. Examples of suitable humectants include, but are not limited to, glycerin, 1,2-propanediol (propylene glycol), 1,3-propanediol, dipropylene glycol, and the like. In some embodiments, the humectant is glycerin.

Tobacco Material

In some embodiments, the oral composition may include a tobacco material. The tobacco material can vary in species, type, and form. Generally, the tobacco material is obtained from for a harvested plant of the *Nicotiana* species. Example *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N.* x *sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis* subsp. Hersperis, *N. pauciflora, N. petunioides, N. quadrivalvis, N. repanda, N. rotundifolia, N. solanifolia*, and *N. spegazzinii*. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

The *Nicotiana* species can, in some embodiments, be selected for the content of various compounds that are present therein. For example, plants can be selected on the basis that those plants produce relatively high quantities of one or more of the compounds desired to be isolated therefrom. In certain embodiments, plants of the *Nicotiana* species (e.g., *Galpao commun* tobacco) are specifically grown for their abundance of leaf surface compounds. Tobacco plants can be grown in greenhouses, growth chambers, or outdoors in fields, or grown hydroponically.

Various parts or portions of the plant of the *Nicotiana* species can be included within a composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material comprises solid tobacco material selected from the group consisting of lamina and stems. The tobacco that is used for the mixture most preferably includes tobacco lamina, or a tobacco lamina and stem mixture (of which at least a portion is smoke-treated). Portions of the tobaccos within the mixture may have processed forms, such as processed tobacco stems (e.g., cut-rolled stems, cut-rolled-expanded stems or cut-puffed stems), or volume expanded tobacco (e.g., puffed tobacco, such as dry ice expanded tobacco (DIET)). See, for example, the tobacco expansion processes set forth in U.S. Pat. No. 4,340,073 to de la Burde et al.; U.S. Pat. No. 5,259,403 to Guy et al.; and U.S. Pat. No. 5,908,032 to Poindexter, et al.; and U.S. Pat. No. 7,556,047 to Poindexter, et al., all of which are incorporated by reference. In addition, the d mixture optionally may incorporate tobacco that has been fermented. See, also, the types of tobacco processing techniques set forth in PCT WO2005/063060 to Atchley et al., which is incorporated herein by reference.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent or less than about 5 weight percent. Most preferably, the tobacco material is employed in the form of parts or pieces that have an average particle size between 1.4 millimeters and 250 microns. In some instances, the tobacco particles may be sized to pass through a screen mesh to obtain the particle size range required. If desired, air classification equipment may be used to ensure that small sized tobacco particles of the desired sizes, or range of sizes, may be collected. If desired, differently sized pieces of granulated tobacco may be mixed together.

The manner by which the tobacco is provided in a finely divided or powder type of form may vary. Preferably, tobacco parts or pieces are comminuted, ground or pulverized into a powder type of form using equipment and techniques for grinding, milling, or the like. Most preferably, the tobacco is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. For example, the tobacco plant or portion thereof can be separated into individual parts or pieces (e.g., the leaves can be removed from the stems, and/or the stems and leaves can be removed from the stalk). The harvested plant or individual parts or pieces can be further subdivided into parts or pieces (e.g., the leaves can be shredded, cut, comminuted, pulverized, milled or ground into pieces or parts that can be characterized as filler-type pieces, granules, particulates or fine powders). The plant, or parts thereof, can be subjected to external forces or pressure (e.g., by being pressed or subjected to roll treatment). When carrying out such processing conditions, the plant or portion thereof can have a moisture content that approximates its natural moisture content (e.g., its moisture content immediately upon harvest), a moisture content achieved by adding moisture to the plant or portion thereof, or a moisture content that results from the drying of the plant or portion thereof. For example, powdered, pulverized, ground or milled pieces of plants or portions thereof can have moisture contents of less than about 25 weight percent, often less than about 20 weight percent, and frequently less than about 15 weight percent.

For the preparation of oral compositions, it is typical for a harvested plant of the *Nicotiana* species to be subjected to a curing process. The tobacco materials incorporated within the oral composition as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and *Galpao* tobaccos), Indian air cured, Red Russian and *Rustica* tobaccos, as well as various other rare or specialty tobaccos and various blends of any of the foregoing tobaccos.

The tobacco material may also have a so-called "blended" form. For example, the tobacco material may include a mixture of parts or pieces of flue-cured, burley (e.g., Malawi burley tobacco) and Oriental tobaccos (e.g., as tobacco composed of, or derived from, tobacco lamina, or a mixture of tobacco lamina and tobacco stem). For example, a representative blend may incorporate about 30 to about 70 parts burley tobacco (e.g., lamina, or lamina and stem), and about 30 to about 70 parts flue cured tobacco (e.g., stem, lamina, or lamina and stem) on a dry weight basis. Other example tobacco blends incorporate about 75 parts flue-cured tobacco, about 15 parts burley tobacco, and about 10 parts Oriental tobacco; or about 65 parts flue-cured tobacco, about 25 parts burley tobacco, and about 10 parts Oriental tobacco; or about 65 parts flue-cured tobacco, about 10 parts burley tobacco, and about 25 parts Oriental tobacco; on a dry weight basis. Other example tobacco blends incorporate about 20 to about 30 parts Oriental tobacco and about 70 to about 80 parts flue-cured tobacco on a dry weight basis.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

In some embodiments, the type of tobacco material is selected such that it is initially visually lighter in color than other tobacco materials to some degree (e.g., whitened or bleached). Tobacco pulp can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. No. 2,148,147 to Baier; U.S. Pat. No. 2,170,107 to Baier; U.S. Pat. No. 2,274,649 to Baier; U.S. Pat. No. 2,770,239 to Prats et al.; U.S. Pat. No. 3,612,065 to Rosen; U.S. Pat. No. 3,851,653 to Rosen; U.S. Pat. No. 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. Nos. 2012/0067361 to Bjorkholm et al.; 2016/0073686 to Crooks; 2017/0020183 to Bjorkholm; and 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein.

Typical inclusion ranges for tobacco materials can vary depending on the nature and type of the tobacco material, and the intended effect on the composition, with an example range of up to about 30% by weight (or up to about 20% by weight or up to about 10% by weight or up to about 5% by weight), based on total weight of the oral composition (e.g., about 0.1 to about 15% by weight). In some embodiments, the oral compositions of the disclosure can be characterized as completely free or substantially free of tobacco material (other than purified nicotine as an active ingredient). For example, certain embodiments can be characterized as having less than 1% by weight, or less than 0.5% by weight, or less than 0.1% by weight of tobacco material, or less than 0.01% by weight of tobacco material, or 0% by weight of tobacco material.

Salt

In some embodiments, the oral composition comprises a salt (e.g., an alkali metal salt), typically employed in an amount sufficient to provide desired sensory attributes to the product. Non-limiting examples of suitable salts include sodium chloride, potassium chloride, ammonium chloride, flour salt, sodium acetate, sodium citrate, and the like.

When present, a representative amount of salt is at least about 0.5% by weight, such as at least about 1% by weight, such as at least about 1.5% by weight. In some embodiments, the oral composition may comprise salt in an amount of from about 0.5% to about 10% by weight, such as from about 1% to about 7.5% by weight, such as from about 1.5% to about 5% by weight, based on the total weight of the oral composition.

Buffering Agent

In certain embodiments, the oral composition may comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Non-limiting examples of suitable buffers include alkali metals acetates, glycinates, phosphates, glycerophosphates, citrates, carbonates, hydrogen carbonates, borates, or mixtures thereof. In some embodiments, the buffering agent is selected from the group consisting of sodium citrate, sodium carbonate, sodium bicarbonate, sodium phosphate, ammonium phosphate, and mixtures thereof. In some embodiments, the buffering agent is sodium citrate.

Where present, the buffering agent is typically present in an amount less than about 5% based on the weight of the composition; for example, from about 0.5% to about 5%, such as, e.g., from about 0.75% to about 4%, from about 0.75% to about 3%, or from about 1% to about 2% by weight, based on the total weight of the oral composition.

Colorants

A colorant may be employed in amounts sufficient to provide the desired physical attributes to the oral composition. Natural or synthetic colorants, such as natural or synthetic dyes, food-grade colorants and pharmaceutical-grade colorants may be used. Examples of colorants include various dyes and pigments, such as caramel coloring and titanium dioxide. Natural colorants such as curcumin, beet juice extract, spirulina; also a variety of synthetic pigments may also be used. In some embodiments, the colorant is a lake dye, such as a red or blue aluminum lake dye. The amount of colorant utilized in the oral composition can vary, but when present is typically up to about 3% by weight, such as from about 0.1%, about 0.5%, or about 1%, to about 3% by weight, based on the total weight of the oral composition.

Oral Care Additives

In some embodiments, the oral composition comprises an oral care ingredient (or mixture of such ingredients). Oral care ingredients provide the ability to inhibit tooth decay or loss, inhibit gum disease, relieve mouth pain, whiten teeth, or otherwise inhibit tooth staining, elicit salivary stimulation, inhibit breath malodor, freshen breath, or the like. For example, effective amounts of ingredients such as thyme oil, eucalyptus oil and zinc (e.g., such as the ingredients of formulations commercially available as ZYTEX® from Discus Dental) can be incorporated into the oral composition. Other examples of ingredients that can be incorporated in desired effective amounts within the present composition can include those that are incorporated within the types of oral care compositions set forth in Takahashi et al., Oral Microbiology and Immunology, 19(1), 61-64 (2004); U.S. Pat. No. 6,083,527 to Thistle; and US Pat. Appl. Pub. Nos. 2006/0210488 to Jakubowski and 2006/02228308 to Cummins et al. Other exemplary ingredients of tobacco containing-formulation include those contained in formulations marketed as MALTISORB® by Roquette and DENTIZYME® by NatraRx. When present, a representative amount of oral care additive is at least about 1%, often at least about 3%, and frequently at least about 5% of the total weight of the composition. The amount of oral care additive within the oral composition will not typically exceed about 30%, often will not exceed about 25%, and frequently will not exceed about 20% of the total weight of the oral composition.

Other Additives

Other additives can be included in the oral composition. For example, the oral composition can be processed, blended, formulated, combined, and/or mixed with other materials or ingredients. The additives can be artificial, or can be obtained or derived from herbal or biological sources. Examples of further types of additives include thickening or gelling agents (e.g., fish gelatin), preservatives (e.g., potassium sorbate, sodium benzoate, calcium propionate, and the like), disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final composition, with an example range of up to about 10% by weight, (e.g., from about 0.1% to about 5% by weight) based on total weight of the composition For example, where present, a preservative (such as potassium sorbate, sodium benzoate, calcium propionate, or the like) can be included in the oral composition in an amount of from about 0.001% to about 5% by weight of the composition, such as from about 0.01% to about 2.5% by weight of the composition, such as from about 0.05% to about 1% by weight of the oral composition.

The aforementioned additives can be employed together (e.g., as additive formulations) or separately (e.g., individual additive components can be added at different stages involved in the preparation of the final oral composition). Furthermore, the aforementioned types of additives may be encapsulated as provided in the final product or composition. Exemplary encapsulated additives are described, for example, in WO2010/132444 to Atchley, which is incorporated by reference herein.

Configured for Oral Use

The oral composition as described herein is configured for oral use. The term "configured for oral use" as used herein means that the oral composition is provided in a form such that during use, saliva in the mouth of the user causes one or more of the components of the oral composition (e.g., flavoring agents and/or active ingredients) to pass into the mouth of the user. In certain embodiments, the oral composition is adapted to deliver components to a user through mucous membranes in the user's mouth, the user's digestive system, or both, and, in some instances, said component is an active ingredient that can be absorbed through the mucous membranes in the mouth or absorbed through the digestive tract when the oral composition is used.

The oral composition as described herein is in a solid, chewable form, meaning the oral composition has a mild resilience or "bounce" upon chewing, and possesses a desirable degree of malleability. Such oral compositions are referred to herein as "chewable," "chews," or "chewing gums." An oral composition in chewable form is generally in the form of a non-dissolving gum in which only certain components (e.g., active ingredients, flavor, bulking agent(s), sweeteners, and the like) dissolve, leaving behind a non-dissolving matrix. As used herein, the terms "dissolve," "dissolving," and "dissolvable" refer to oral compositions having aqueous-soluble components (e.g., active ingredients, flavor, bulking agent(s), sweeteners, and the like) that interact with moisture in the oral cavity and enter into solution, thereby causing gradual consumption of at least a portion of the oral composition. The desired textural properties of such an oral composition in chewable form may include one or more of adhesiveness, cohesiveness, density, graininess, gumminess, hardness, heaviness, moisture absorption, moisture release, mouth coating, roughness, slipperiness, smoothness, viscosity, and wetness. In some embodiments, the oral composition comprises a coating as described herein below, which may serve to provide additional properties to the oral composition (e.g., crunchiness, immediate release of certain components, additional flavors and or active ingredients).

The physical format of the oral composition may vary. For example, the oral composition may be in a tablet form (such as a compressed tablet) having any desired shape, or may be in the form of a sheet of any desired dimension (thickness, width, and length). In some embodiments, the oral composition will be in a form of a conventional stick (i.e., having a length greater than a width, and a thickness substantially less than either the length or width), or a tablet in any desired shape, such as a substantially square or round format of any desired thickness.

In some embodiments, the oral composition comprises an outer coating. An outer coating may be hard, soft, in the form of a film, or any combination thereof. The coating may comprise from about 0.1 to about 75% by weight of a coated oral composition. In some embodiments, the oral composition comprises an outer coating in the form of a film. Such film coatings may be provided by film-forming agents such as cellulose derivatives, modified starches, dextrin, gelatin, zein, shellac, gums (e.g., gum arabic or vegetable gums), waxes, synthetic polymers, or combinations thereof. In some embodiments, the oral composition comprises an outer coating in the form of a hard coating. Hard coatings provide a sweet, crunchy layer, which may further serve to protect the softer gum center. Hard coatings may be sugar based or sugar free. Suitable hard coatings may comprise one or more sugars, such as sucrose or dextrose, or one or more sugar alcohols, such as sorbitol, maltitol, mannitol, xylitol, erythritol, lactitol, isomalt, and the like. In some embodiments, the coating comprises isomalt.

In some embodiments, the coating further comprises a flavoring agent, which may be the same or different from any flavoring agent provided in the oral composition, an active ingredient, which may be the same or different from any active ingredient provided in the oral composition, a colorant, or combinations of any thereof. In embodiments comprising a coating including an active ingredient, a flavorant, or both, the coated oral composition may provide instant, delayed, extended, and/or separate delivery of e.g., various flavors and active ingredients.

Preparation of the Oral Composition

Generally, an oral composition as disclosed herein is prepared by combining the various components of the oral composition (e.g., gum base, bulking agent, active ingredient, flavorant, and the like) to provide a homogenous mixture. The manner by which the various components of the oral composition (e.g., gum base, bulking agent, active ingredient, flavorant, and the like) are combined may vary. Generally, the gum base is combined with the bulking agent, the active ingredient and/or flavorant, the humectant, and any further components of the composition, followed by mixing.

The various components of the oral composition may be contacted, combined, or mixed together using any mixing technique or equipment known in the art. Any mixing method that brings the oral composition ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference.

In some embodiments, the gum base is warmed before combining with the other components in order to facilitate mixing. For example, the gum base may be heated by any appropriate means (steam kettle, oven, microwave irradiation, etc.) for a sufficient period of time and at an appropriate temperature, such that the gum base becomes soft and malleable. In some embodiments, the gum base is heated to a temperature from about 50 to about 100° C., such as from about 70 to about 90° C. In some embodiments, such heating is achieved by microwave heating for a period of time, such as from about 1 minute to about 10 minutes. The warm gum base is typically mixed for a period of time sufficient to ensure uniformity and a smooth consistency.

The remaining oral composition components may then be added, sequentially or simultaneously, followed by mixing. In particular embodiments, solid (e.g., dry or particulate) ingredients and liquid (e.g., wet or in solution form) ingredients are added separately. For example, in some embodiments, the wet components (e.g., bulking agents in liquid form, active ingredient in solution form, humectant, etc.) are mixed with each other to form a liquid mix, and a portion of the liquid mix is added, followed by mixing. Subsequently, the dry components (e.g., bulking agent(s), organic acid, etc.) are mixed together to form a dry mix, and a portion of the dry mix is added, followed by mixing. This alternating addition is repeated until all components have been added. In a particular embodiment, approximately ⅓ of the liquid mix is added in each addition, and approximately ⅓ of the dry mix is added in each addition. In some embodiments, the active ingredient (e.g., nicotine or a nicotine salt) is added separately from the wet or dry mix. In some embodiments, the sweetener is added separately from the wet or dry mix. In some embodiments, the sweetener is not part of the dry mix, but is added with the first portion thereof. In some embodiments, the composition comprises nicotine polacrilex, and the nicotine polacrilex is added with one or more portions of the dry ingredient mix. In some embodiments, the flavoring agent is not part of the wet or the dry mix, and is added after all the dry and wet components have been incorporated. Without wishing to be bound by any particular theory, it is believed that portion-wise addition, and separate addition of sweetener and flavoring agent, may provide a more extended and uniform delivery of sweetener and/or flavor during consumption of the oral composition.

In some embodiments, the organic acid component is an alkali metal salt of an organic acid, such as sodium benzoate. In some embodiments, the organic acid component (e.g., sodium benzoate) is added to the mixture after all the dry and wet components have been incorporated, but prior to addition of the flavoring agent(s).

In some embodiments, the composition further comprises flavor granules as described herein above. Such granules may generally be prepared by creating a flavor mix, combining the flavor mix with glycerin (or other humectant) and isomalt (or other sugar alcohol), mixing thoroughly, and extruding through a die. In some embodiments, the flavor mix is prepared by combining a filler such as microcrystalline cellulose, a colorant (e.g., a red or blue dye, such as a lake), and one or more flavorants and sweeteners (e.g., a non-caloric sweetener such as sucralose). The mix is then extruded through a die (e.g., a 0.5 to 1.5 mm die) to form beads, which may optionally be spheronized. The beads generally have a size in a range of about 14 to 20 mesh, or about 0.5 to about 1.5 mm. In other embodiments, the flavor granules are prepared by combining one or more sugar alcohols (e.g., isomalt, maltitol, or a combination thereof), a sweetener (e.g., a non-caloric sweetener such as sucralose), and a colorant (e.g., a red or blue dye, such as a lake), and one or more flavorants, heating the mix to a liquid state, cooling to form a solid mass, breaking or crushing the solid mass into particles, and sieving the particles to provide granules of the desired size. The flavor granules (beads or particulate) are generally incorporated into the composition as is (e.g., without drying or further processing), optionally together with another flavorant. After addition of the granules, the composition is mixed for a period of time sufficient to distribute the components evenly throughout the composition. Typically, about 45 seconds of mixing is required.

The entire mixing process for preparation of the composition typically takes from about five minutes to about 30 minutes, depending on batch size. Those skilled in the art will recognize that variations of this mixing procedure, or other mixing procedures, may be followed.

Following the mixing, the oral composition is discharged from the mixer. The oral composition may be dusted with various substances to aid in processing (for example, to reduce stickiness) or alter the initial taste properties of the oral composition. Such substances may include sucrose, mannitol, starch, calcium carbonate, talc, lactitol, lactose, and combinations thereof. The oral composition is then extruded, rolled, compressed, or the like. In some embodiments, the oral composition is processed through a sheeter to provide the desired thickness. For example, the oral gum base may undergo multiple passages through at least one and preferably several sets of counter-rotating reducing rollers and finishing rollers to elongate and decrease the thickness of the oral composition. For stick gum, this thickness generally ranges from about 0.05 to about 0.10 inches, such as from about 0.06 to about 0.08 inches, and for tablet gum, this may range from about 0.15 to about 0.3 inches, such as from about 0.18 to 0.25 inches. In some embodiments, the oral composition may undergo further processing, such as drying, curing, aging, or the like. The oral composition is then packaged in the desired format.

EXAMPLES

Aspects of the present invention are more fully illustrated by the following examples, which are set forth to illustrate certain aspects of the present invention and are not to be construed as limiting thereof.

Example 1. Preparation of Flavored Chewing Gum with Nicotine Benzoate

Chewing gum tablets containing a flavoring agent and approximately 2 mg each of nicotine were prepared using the formulation components provided in Table 2.

Sorbitol, isomalt, and sodium benzoate were combined to give a dry mixture. Separately, maltitol syrup, glycerin, and nicotine benzoate solution were combined to form a liquid mixture. The gum base (Artica T; CAFOSA Gum S/A, Barcelona, Spain) was warmed in a microwave oven under low power for approximately five minutes to soften. The heated, softened gum base was mixed by hand until uniform and transferred to the bowl of a commercial mixer. Approximately ⅓ of the liquid mixture was added to the gum base followed by two minutes of mixing. Approximately ⅓ of the dry mixture, along with sucralose, was added to the gum base-liquid mixture followed by two minutes of mixing. Additions of the dry and liquid mixtures were each repeated twice, followed in each case by a further two minutes of mixing to incorporate the remaining dry and liquid mixtures. The flavoring agent was added to the mixture followed by mixing for 45 seconds. The mixture was removed from the mixer bowl and dusted with mannitol powder, then run through a sheeter to provide a uniform thickness of the composition. Square tablets weighing 1.65 g each were die punched from the composition sheet.

TABLE 2

Oral gum composition components and amounts

| Component | % by Weight, based on the total weight of oral gum composition |
|---|---|
| gum base | 20-30 |
| sorbitol | 29-43 |
| maltitol (75% aqueous) | 12-18 |
| isomalt | 12-18 |
| glycerin | 1.2-1.8 |
| sucralose | 0.3-0.6 |
| flavoring agent | 2-4 |
| nicotine benzoate (12% aqueous solution) | 0.8-1.2 |
| sodium benzoate | 1-6 |
| mannitol | 0.8-1.2 |

Example 2. Preparation of Colored Flavor Granules

Colored flavoring granules (red and blue) were prepared using the formulation components provided in Table 3.

Microcrystalline cellulose, colorant (either red or blue lake dye), and flavor were combined and mixed to form a flavor mix. To this mix was added glycerin and isomalt, followed by mixing to obtain a homogenous composition. The homogenous composition was then extruded through a 1.5 mm die to form beads having a size of 14 to 20 mesh. The beads were used directly in the following Examples.

TABLE 3

Flavor granule components and amounts

| Component | % by Weight, based on the total weight of flavor granules |
|---|---|
| isomalt | 60-90 |
| glycerin | 16-22 |
| sucralose | 0.1-0.5 |
| microcrystalline cellulose | 1-3 |
| colorant | 0.1-0.5 |
| flavor | 1-3 |

Example 3. Preparation of Flavored Chewing Gum with Nicotine Benzoate and Flavor Granules Chewing gum tablets containing a flavoring agent and approximately 2 mg each of nicotine were prepared using the formulation components provided in Table 4.

The gum base (Artica T; CAFOSA Gum S/A, Barcelona, Spain) was warmed in a microwave oven under low power for approximately five minutes to soften. Separately, maltitol syrup and glycerin were combined to form a liquid mixture. Separately, sorbitol and isomalt were combined to give a dry mixture.

The heated, softened gum base was mixed by hand until uniform and transferred to the bowl of a commercial mixer. Approximately ⅓ of the liquid mixture was added to the gum base, along with the nicotine benzoate solution, followed by two minutes of mixing. Approximately ⅓ of the dry mixture, along with the sucralose, was added through a 20-mesh sieve to the gum base-liquid mixture, followed by two minutes of mixing. Additions of the liquid and dry mixtures were each repeated twice, followed in each case by a further two minutes of mixing to incorporate the remaining dry and liquid mixtures. Sodium benzoate was added to the mixture, followed by the flavoring agent and flavor granules (Example 2) were added to the mixture, followed by mixing for 45 seconds. The mixture was removed from the mixer bowl and dusted with mannitol powder, then run through a sheeter to provide a uniform thickness of the composition. The total batch weight was 2 kg. Square tablets weighing 1.74 g each were die punched from the composition sheet.

TABLE 4

Oral gum composition components and amounts

| Component | % by Weight, based on the total weight of oral gum composition |
|---|---|
| gum base | 20-30 |
| sorbitol | 29-43 |
| maltitol (75% aqueous) | 12-18 |
| isomalt | 12-18 |
| glycerin | 1.2-1.8 |
| sucralose | 0.3-0.6 |
| nicotine benzoate (12% aqueous solution) | 0.8-1.2 |
| sodium benzoate | 0.8-1.2 |
| flavoring agent | 1.2-1.8 |
| red flavor granules | 0.8-1.2 |
| blue flavor granules | 0.8-1.2 |
| mannitol | 0.8-1.2 |

Example 4. Preparation of Flavored Chewing Gum with Nicotine Benzoate, Nicotine Polacrilex, and Flavor Granules Chewing gum tablets containing a flavoring agent and approximately 2 mg each of nicotine (equal parts of the nicotine from nicotine benzoate and nicotine polacrilex) were prepared using the formulation components provided in Table 5.

The gum base (Artica T; CAFOSA Gum S/A, Barcelona, Spain) was warmed in a microwave oven under low power for approximately five minutes to soften. Separately, maltitol syrup and glycerin were combined to form a liquid mixture. Separately, sorbitol and isomalt were combined to give a dry mixture.

The heated, softened gum base was mixed by hand until uniform and transferred to the bowl of a commercial mixer. Approximately ⅓ of the liquid mixture was added to the gum base, along with the nicotine benzoate solution, followed by two minutes of mixing. Approximately ⅓ of the dry mixture, along with the sucralose and nicotine polacrilex, was added through a 20-mesh sieve to the gum base-liquid mixture, followed by two minutes of mixing. Additions of the liquid and dry mixtures were each repeated twice, followed in each case by a further two minutes of mixing to incorporate the remaining dry and liquid mixtures. Sodium benzoate was added to the mixture, followed by the flavoring agent and flavor granules (Example 2) were added to the mixture, followed by mixing for 45 seconds. The mixture was removed from the mixer bowl and dusted with mannitol powder, then run through a sheeter to provide a uniform thickness of the composition. The total batch weight was 2 kg. Square tablets weighing 1.74 g each were die punched from the composition sheet.

TABLE 5

Oral gum composition components and amounts

| Component | % by Weight, based on the total weight of oral gum composition |
|---|---|
| gum base | 20-30 |
| sorbitol | 29-43 |
| maltitol (75% aqueous) | 12-18 |
| isomalt | 12-18 |
| glycerin | 1.2-1.8 |
| sucralose | 0.3-0.6 |
| nicotine benzoate (12% aqueous solution) | 0.4-0.6 |
| nicotine polacrilex | 0.2-0.4 |
| sodium benzoate | 0.8-1.2 |
| flavoring agent | 1.2-1.8 |
| red flavor granules | 0.8-1.2 |
| blue flavor granules | 0.8-1.2 |
| mannitol | 0.8-1.2 |

Example 5. Preparation of Flavored Chewing Gum with Nicotine Polacrilex and Flavor Granules Chewing gum tablets containing a flavoring agent and approximately 2 mg each of nicotine (from nicotine polacrilex) were prepared using the formulation components provided in Table 6.

The gum base (Artica T; CAFOSA Gum S/A, Barcelona, Spain) was warmed in a microwave oven under low power for approximately five minutes to soften. Separately, maltitol syrup and glycerin were combined to form a liquid mixture. Separately, sorbitol and isomalt were combined to give a dry mixture.

The heated, softened gum base was mixed by hand until uniform and transferred to the bowl of a commercial mixer. Approximately ⅓ of the liquid mixture was added to the gum base followed by two minutes of mixing. Approximately ⅓ of the dry mixture, along with the sucralose and nicotine polacrilex, was added through a 20-mesh sieve to the gum base-liquid mixture, followed by two minutes of mixing. Additions of the liquid and dry mixtures were each repeated twice, followed in each case by a further two minutes of mixing to incorporate the remaining dry and liquid mixtures. Sodium benzoate was added to the mixture, followed by the flavoring agent and flavor granules (Example 2) were added to the mixture, followed by mixing for 45 seconds. The mixture was removed from the mixer bowl and dusted with mannitol powder, then run through a sheeter to provide a uniform thickness of the composition. The total batch weight was 2 kg. Square tablets weighing 1.74 g each were die punched from the composition sheet.

TABLE 6

| Oral gum composition components and amounts | |
|---|---|
| Component | % by Weight, based on the total weight of oral gum composition |
| gum base | 20-30 |
| sorbitol | 29-43 |
| maltitol (75% aqueous) | 12-18 |
| isomalt | 12-18 |
| glycerin | 1.2-1.8 |
| sucralose | 0.3-0.6 |
| nicotine polacrilex | 0.5-0.7 |
| sodium benzoate | 0.8-1.2 |
| flavoring agent | 1.2-1.8 |
| red flavor granules | 0.8-1.2 |
| blue flavor granules | 0.8-1.2 |
| mannitol | 0.8-1.2 |

Example 6. Preparation of Colored Flavor Granules with Reduced Size

Colored flavoring granules (red and blue) were prepared using the formulation components provided in Table 7.

Microcrystalline cellulose, colorant (either red or blue lake dye), and flavor were combined and mixed to form a flavor mix. To this mix was added glycerin and isomalt, followed by mixing to obtain a homogenous composition. The homogenous composition was then extruded through a 0.5 mm die to form beads, which were then spheronized and sieved to provide beads of the desired size.

TABLE 7

| Flavor granule components and amounts | |
|---|---|
| Component | % by Weight, based on the total weight of flavor granules |
| isomalt | 60-90 |
| glycerin | 16-22 |
| sucralose | 0.1-0.5 |
| microcrystalline cellulose | 1-3 |
| colorant | 0.1-0.5 |
| flavor | 1-3 |

Example 7. Alternative Preparation of Colored Flavor Granules

Colored flavoring granules (red and blue) were prepared using the formulation components provided in Table 8.

Isomalt, maltitol syrup, colorant (either red or blue lake dye), sucralose, and flavor were combined and heated with mixing to form a fluid, liquid mixture. The liquid mixture was then cooled to form a solid mass, which was crushed and sieved to provide flavor particles having the desired particle size range (approximately 0.5 mm).

TABLE 8

| Flavor granule components and amounts | |
|---|---|
| Component | % by Weight, based on the total weight of flavor granules |
| isomalt | 92-96 |
| maltitol syrup | 4-6 |
| sucralose | 0.1-0.5 |
| colorant | 0.5-1.5 |
| flavor | 0.1-1 |

Example 8. Alternative Preparation of Colored Flavor Granules—High Flavor Load

Colored flavoring granules are prepared using the formulation components provided in Table 9.

Microcrystalline cellulose, colorant (either red or blue lake dye), and flavor are combined and mixed to form a flavor mix. To this mix is added glycerin and isomalt, followed by mixing to obtain a homogenous composition. The homogenous composition is then extruded through a 0.5 mm die to form beads, which are then spheronized and sieved to provide beads of the desired size.

TABLE 9

| Flavor granule components and amounts | |
|---|---|
| Component | % by Weight, based on the total weight of flavor granules |
| isomalt | 15-35 |
| glycerin | 15-30 |
| sucralose | 0.1-0.5 |
| microcrystalline cellulose | 20-50 |
| colorant | 0.1-0.5 |
| flavor | 20-30 |

The invention claimed is:

1. An oral composition comprising:

a gum base;

one or more bulking agents;

an active ingredient having a basic amine functionality; and a combination of an organic acid having a logP value from about 1 to about 12, and an alkali metal salt of an organic acid having a logP value from about 1 to about 12, wherein at least a portion of the active ingredient having the basic amine functionality is associated with at least a portion of the organic acid or the alkali metal salt thereof, the association in the form of an ion pair between the basic amine and a conjugate base of the organic acid.

2. The oral composition of claim 1, in the form of a chewing gum.

3. The oral composition of claim 1, wherein the organic acid has a logP value of from about 1.4 to about 4.5.

4. The oral composition of claim 1, wherein the organic acid has a logP value of from about 2.5 to about 3.5.

5. The oral composition of claim 1, wherein the organic acid has a logP value of from about 4.5 to about 12, and wherein the composition further comprises a solubility enhancer.

6. The oral composition of claim 5, wherein the solubility enhancer is glycerol or propylene glycol.

7. The oral composition of claim 1, comprising from about 0.05, about 0.1, about 1, about 1.5, about 2, or about 5, to about 10, about 15, or about 20 molar equivalents of the organic acid, the alkali metal salt thereof, or the combination thereof, relative to the active ingredient having a basic amine functionality, calculated as the amine free base.

8. The oral composition of claim 1, comprising from about 2 to about 10 molar equivalents of the organic acid, the alkali metal salt thereof, or the combination thereof, relative to the active ingredient having a basic amine functionality, calculated as the amine free base.

9. The oral composition of claim 1, wherein the organic acid comprises benzoic acid, a menthyl or tocopherol monoester of a dicarboxylic acid, or a combination thereof.

10. The oral composition of claim 9, wherein the dicarboxylic acid is malonic acid, succinic acid, glutaric acid, adipic acid, fumaric acid, maleic acid, or a combination thereof.

11. The oral composition of claim 1, wherein the organic acid comprises tocopherol succinate, monomenthyl succinate, monomenthyl fumarate, monomenthyl glutarate, or a combination thereof.

12. The oral composition of claim 11, further comprising benzoic acid and sodium benzoate.

13. The oral composition of claim 1, wherein the organic acid is benzoic acid and the salt thereof is sodium benzoate.

14. The oral composition of claim 1, wherein the alkali metal is sodium or potassium.

15. The oral composition of claim 1, wherein a ratio of the organic acid to the alkali metal salt of the organic acid is from about 0.1 to about 10.

16. The oral composition of claim 1, wherein a pH of the composition is from about 4.0 to about 9.0.

17. The oral composition of claim 1, wherein a pH of the composition is from about 4.5 to about 7.

18. The oral composition of claim 1, wherein a pH of the composition is from about 5.5 to about 7.

19. The oral composition of claim 1, wherein a pH of the composition is from about 4.0 to about 5.5.

20. The oral composition of claim 1, wherein a pH of the composition is from about 7.0 to about 9.0.

21. The oral composition of claim 1, wherein the active ingredient having a basic amine functionality is nicotine.

22. The oral composition of claim 21, wherein the nicotine is present in an amount of from about 0.001 to about 10% by weight of the composition, calculated as the free base and based on the total weight of the composition.

23. The oral composition of claim 21, wherein a portion of the nicotine is present as a salt, with the organic acid, as nicotine polacrilex, or a combination thereof.

24. The oral composition of claim 1, wherein the gum base comprises a synthetic elastomer.

25. The oral composition of claim 24, wherein the gum base further comprises a plasticizer, a filler, a softener, an emulsifier, a wax, an anti-tacking agent, an antioxidant, or a combination thereof.

26. The oral composition of claim 1, wherein the bulking agent comprises one or more sugar alcohols.

27. The oral composition of claim 1, wherein the oral composition comprises, as the bulking agent, a combination of:

sorbitol in an amount from about 25 to about 50% by weight;

maltitol in an amount from about 10 to about 20% by weight; and isomalt in an amount from about 10 to about 20% by weight, each based on the total weight of the oral composition.

28. The oral composition of claim 1, further comprising one or more additional active ingredients, one or more flavoring agents, one or more salts, one or more sweeteners, one or more humectants, a tobacco material, or combinations thereof.

29. The oral composition of claim 1, further comprising one or more additional active ingredients selected from the group consisting of nutraceuticals, botanicals, stimulants, amino acids, vitamins, cannabinoids, cannabimimetics, and terpenes.

30. The oral composition of claim 1, comprising:

the gum base in an amount from about 20 to about 30% by weight, based on the total weight of the oral composition;

the bulking agent in an amount from about 50 to about 80% by weight, based on the total weight of the oral composition, wherein the bulking agent comprises one or more sugar alcohols;

a humectant in an amount from about 1 to about 2% by weight, based on the total weight of the oral composition;

nicotine benzoate; and sodium benzoate.

31. The oral composition of claim 30, further comprising nicotine polacrilex.

32. The oral composition of claim 1, further comprising flavor granules.

33. The oral composition of claim 32, wherein the flavor granules comprise:

a sugar alcohol in an amount by weight from about 60 to about 90%;

a humectant in an amount by weight from about 16 to about 22%;

a sweetener in an amount by weight from about 0.1 to about 0.5%;

a filler in an amount by weight from about 1 to about 3%;

a colorant; and a flavorant, wherein each amount by weight is based on the total weight of the flavor granules.

34. The oral composition of claim 32, wherein the flavor granules comprise:

a sugar alcohol in an amount by weight from about 15 to about 35%;

a filler in an amount by weight from about 20 to about 50%;

a flavorant in an amount by weight from about 20 to about 30%;

a humectant in an amount by weight from about 15 to about 30%;

a sweetener in an amount by weight from about 0.1 to about 0.5%; and a colorant in an amount by weight from about 0.1 to about 1.5%, wherein each amount by weight is based on the total weight of the flavor granules.

35. The oral composition of claim 34, wherein the sugar alcohol is isomalt, the filler is microcrystalline cellulose, the humectant is glycerin, and the sweetener is sucralose.

36. The oral composition of claim 32, wherein the flavor granules comprise:

a combination of two sugar alcohols in a total amount by weight from about 96 to about 99%;

a sweetener in an amount by weight from about 0.1 to about 0.5%; and a colorant and a flavorant comprising the remainder of the flavor granules.

37. The oral composition of claim 36, wherein the flavor granules consist of:

isomalt in an amount by weight from about 92 to about 96%;

maltitol syrup in an amount by weight from about 4 to about 6%;

sucralose in an amount by weight from about 0.1 to about 0.5%; and the balance consists of colorant and flavorant.

38. The oral composition of claim 1, wherein the organic acid and the salt of the organic acid both comprise the same organic acid.

39. The oral composition of claim 1, wherein the organic acid and the salt of the organic acid each comprise a different organic acid.

* * * * *